(12) United States Patent
Nahrendorf et al.

(10) Patent No.: US 9,624,307 B2
(45) Date of Patent: Apr. 18, 2017

(54) FACTOR XII INHIBITORS FOR THE TREATMENT OF SILENT BRAIN ISCHEMIA AND ISCHEMIA OF OTHER ORGANS

(75) Inventors: Matthias Nahrendorf, Charlestown, MA (US); Ralph Weissleder, Peabody, MA (US); Gerhard Dickneite, Marburg (DE); Guido Stoll, Rimpar (DE); Marc Nolte, Lahntal (DE)

(73) Assignees: The General Hospital Corporation, Boston, MA (US); CSL Behring GmbH, Marburg (DE)

( * ) Notice: Subject to any disclaimer, the term of this patent is extended or adjusted under 35 U.S.C. 154(b) by 0 days.

(21) Appl. No.: 14/003,963

(22) PCT Filed: Mar. 9, 2012

(86) PCT No.: PCT/EP2012/054142
§ 371 (c)(1),
(2), (4) Date: Nov. 18, 2013

(87) PCT Pub. No.: WO2012/120124
PCT Pub. Date: Sep. 13, 2012

(65) Prior Publication Data
US 2014/0072572 A1 Mar. 13, 2014

Related U.S. Application Data

(60) Provisional application No. 61/457,360, filed on Mar. 9, 2011, provisional application No. 61/496,746, filed on Jun. 14, 2011.

(30) Foreign Application Priority Data

Mar. 9, 2011 (EP) .................................. 11157555

(51) Int. Cl.
| | | |
|---|---|---|
| A61K 38/48 | (2006.01) | |
| C07K 14/81 | (2006.01) | |
| C07K 16/40 | (2006.01) | |
| A61K 38/55 | (2006.01) | |
| A61K 38/57 | (2006.01) | |
| A61K 49/00 | (2006.01) | |
| A61K 49/14 | (2006.01) | |
| G01N 33/50 | (2006.01) | |
| A61K 39/395 | (2006.01) | |
| C07K 16/36 | (2006.01) | |

(52) U.S. Cl.
CPC .......... *C07K 16/40* (2013.01); *A61K 38/556* (2013.01); *A61K 38/57* (2013.01); *A61K 39/3955* (2013.01); *A61K 49/0004* (2013.01); *A61K 49/0008* (2013.01); *A61K 49/14* (2013.01); *C07K 14/811* (2013.01); *C07K 16/36* (2013.01); *G01N 33/5088* (2013.01); *A61K 38/4846* (2013.01); *C07K 14/8114* (2013.01); *G01N 2500/10* (2013.01)

(58) Field of Classification Search
None
See application file for complete search history.

(56) References Cited

U.S. PATENT DOCUMENTS

| | | |
|---|---|---|
| 4,383,219 A | 5/1983 | Kaplan |
| 6,403,077 B1 | 6/2002 | Strom et al. |
| 6,613,890 B2 | 9/2003 | White et al. |
| 2003/0219430 A1 | 11/2003 | Faerman et al. |
| 2004/0087778 A1 | 5/2004 | Feige et al. |
| 2005/0059660 A1 | 3/2005 | Fox et al. |
| 2010/0317848 A1 | 12/2010 | Han et al. |

FOREIGN PATENT DOCUMENTS

| | | |
|---|---|---|
| WO | WO 97/07731 A2 | 3/1997 |
| WO | WO 97/07731 A3 | 3/1997 |
| WO | WO 99/36439 A1 | 7/1999 |
| WO | WO 01/79271 A1 | 10/2001 |
| WO | WO 03/076567 A2 | 9/2003 |
| WO | WO 2004/100982 A1 | 11/2004 |
| WO | WO 2004/101740 A2 | 11/2004 |
| WO | WO 2005/000892 A2 | 1/2005 |
| WO | WO 2005/001025 A2 | 1/2005 |
| WO | WO 2005/024044 A2 | 3/2005 |
| WO | WO 2005/063808 A1 | 7/2005 |
| WO | WO 2006/000448 A2 | 1/2006 |
| WO | WO 2006/066878 A1 | 6/2006 |
| WO | WO 2007/073186 A2 | 6/2007 |
| WO | WO 2007/073186 A3 | 6/2007 |
| WO | WO 2007/112986 A1 | 10/2007 |
| WO | WO 2008/098720 A1 | 8/2008 |

(Continued)

OTHER PUBLICATIONS

Kannemeier et al., "Extracellular RNA constitutes a natural procoagulant cofactor in blood coagulation" PNAS, 2007, pp. 6388-6393.*
Knipp et al. "Small ischemic brain lesions after cardiac valve replacement detected by diffusion-weighted magnetic resonance imaging: relative to neurocognitive function", European Journal of Cardio-thoracic Surgery, 2005, pp. 88-96.*
Rosenkranz et al., "The Amount of Solid Cerebral Microemboli during Carotid Stenting Does Not Relate to the Frequency of Silent Ischemic Lesions", Am J Neuroradiol, 2006, pp. 157-161.*

(Continued)

*Primary Examiner* — Lianko Garyu
(74) *Attorney, Agent, or Firm* — Finnegan, Henderson, Farabow, Garrett & Dunner, LLP

(57) ABSTRACT

Silent brain ischemia (SBI) or ischemia of other organs can result from an embolism that is introduced into the arterial system during a medical procedure. The application provides a method of administering a FXII inhibitor in a patient receiving a medical procedure and animal models useful for studying ischemia including SBI and ischemia in other organs, and for evaluating candidate therapeutics.

13 Claims, 10 Drawing Sheets

(56) References Cited

FOREIGN PATENT DOCUMENTS

| | | |
|---|---|---|
| WO | WO 2009/067660 A2 | 5/2009 |
| WO | WO 2009/067660 A3 | 5/2009 |
| WO | WO 2010/049423 A1 | 5/2010 |

OTHER PUBLICATIONS

Liistro et al., "Carotid Artery Stenting", Heart, 2003, pp. 944-948.*
Hagedorn et al , "In Vivo antithrombotic effect of a novel coagulation factor XIIa inhibitor in murine arterial thrombosis and stroke," Hsmostaseologie, 30(1)-A98, p. 15-11 (2010).*
Beattie, W. et al.; "Structure and evolution of human α-fetoprotein deduced from partial sequence of cloned cDNA"; Gene; vol. 20; 1982; pp. 415-422.
Bendszus, M. et al.; "Heparin and Air Filters Reduce Embolic Events Caused by Intra-Arterial Cerebral Angiography: A Prospective, Randomized Trial"; Circulation; vol. 110; Oct. 4, 2004; pp. 2210-2215.
Bendszus, M. et al.; "Silent cerebral ischaemia: hidden fingerprints of invasive medical procedures"; Lancet Neurol.; vol. 5; 2006; pp. 364-372.
Bendszus, M. et al.; "Silent embolism in diagnostic cerebral angiography and neurointerventional procedures: a prospective study"; Lancet; vol. 354, No. 9190; Nov. 6, 1999; pp. 1594-1597.
Breckwoldt, M.O. et al.; "Tracking the inflammatory response in stroke in vivo by sensing the enzyme myeloperoxidase"; PNAS; vol. 105; Nov. 25, 2008; pp. 18584-18589.
Campos, I.T.N. et al.; "Infestin, a thrombin inhibitor presents in *Triatoma infestans* midgut, a Chagas' disease vector: gene cloning, expression and characterization of the inhibitor"; Insect Biochem. Mol. Bio.; vol. 32; 2002; pp. 991-997.
Campos, I.T.N. et al.; "Identification and characterization of a novel factor XIIa inhibitor in the hematophagous insect, *Triatoma infestans* (Hemiptera: Reduviidae)"; FEBS Lett.; vol. 577; 2004; pp. 512-516.
Chen, J.W. et al.; "Imaging of Myeloperoxidase in Mice by Using Novel Amplifiable Paramagnetic Substrates"; Radiology; vol. 240, No. 2; Aug. 2006; pp. 473-481.
Chen, J.W. et al.; "Myeloperoxidase-targeted imaging of active inflammatory lesions in murine experimental autoimmune encephalomyelitis"; Brain; vol. 131; 2008; pp. 1123-1133.
Chen,. Z.Y. et al.; "Inhibition of Plant-Pathogenic Fungi by a Corn Trypsin Inhibitor Overexpressed in *Escherichia coli*"; Applied and Environmental Microbiology; vol. 65, No. 3; Mar. 1999; pp. 1320-1324.
Colman, R.W. et al.; "Hemostasis and Thrombosis. Basic Principles and Clinical Practice"; Fourth Edition; Chapter 6; Lippincott Williams & Wilkins; Philadelphia, Pennsylvania; 2001; pp. 103-121.
Cooke, E. et al.; "Serum Vitamin D-binding Protein is a Third Member of the Albumin and Alpha Fetoprotein Gene Family"; J. Clin. Invest.; vol. 76; Dec. 1985; pp. 2420-2424.
Devereux, J. et al.; "A comprehensive set of sequence analysis programs for the VAX"; Nucleic Acids Research; vol. 12, No. 1; 1984; pp. 387-395.
Hagedorn, I. et al.; "Factor XIIa Inhibitor Recombinant Human Albumin Infestin-4 Abolishes Occlusive Arterial Thrombus Formation Without Affecting Bleeding"; Circulation; vol. 121; Mar. 22, 2010; pp. 1510-1517.
Isawa, H. et al.; "A mosquito salivary protein inhibits activation of the plasma contact system by binding to factor XII and high molecular weight kininogen"; J. Biol. Chem.; vol. 277, No. 31; Aug. 2, 2002; pp. 27651-27658.
Kibbe, A., et al.; "Handbook of Pharmaceutical Excipients"; Third Edition; Pharmaceutical Press; London; 2000; book review, in J. Controlled Release; vol. 71; 2001; pp. 352-352.
Kleinschnitz, C. et al.; "Targeting coagulation factor XII provides protection from pathological thrombosis in cerebral ischemia without interfering with hemostasis"; J. Exp. Med.; vol. 203; 2006; pp. 513-518.
Kobayashi, S. et al.; "Subcortical Silent Brain Infarction as a Risk Factor for Clinical Stroke"; Stroke; vol. 28; Oct. 1997; pp. 1932-1939.
Laskowski, M. et al.; "Protein Inhibitors of Proteinases"; Ann. Rev. Biochem.; vol. 49; 1980; pp. 593-626.
Lichenstein, H. et al.; "Afamin Is a New Member of the Albumin, α-Fetoprotein, and Vitamin D-binding Protein Gene Family"; J. Biol. Chem.; vol. 269, No. 27; Jul. 8, 1994; pp. 18149-18154.
Lopez, O.L. et al.; "Risk Factors for Mild Cognitive Impairment in the Cardiovascular Health Study Cognition Study"; Arch. Neurol.; vol. 60; Oct. 2003; pp. 1394-1399.
Nahrendorf, M. et al.; "Factor XIII Deficiency Causes Cardiac Rupture, Impairs Wound Healing, and Aggravates Cardiac Remodeling in Mice With Myocardial Infarction"; Circulation; vol. 113; Feb. 27, 2006; pp. 1196-1202.
Nahrendorf, M. et al.; "Activatable Magnetic Resonance Imaging Agent Reports Myeloperoxidase Activity in Healing Infarcts and Noninvasively Detects the Antiinflammatory Effects of Atorvastatin on Ischemia-Reperfusion Injury"; Circulation; vol. 11; Feb. 11, 2008; pp. 1153-1160.
Pysz, M.A. et al.; "Molecular imaging: current status and emerging strategies"; Clinical Radiology; vol. 65; 2010; pp. 500-516.
Querol, M. et al.; "A paramagnetic contrast agent with myeloperoxidase-sensing properties"; Organic and Biomolecular Chemistry; vol. 4; 2006; pp. 1887-1895.
Ratnoff, O.D. et al.; "A Familial Hemorrhagic Trait Associated With a Deficiency of a Clot-Promoting Fraction of Plasma"; J. Clin. Invest.; vol. 34; 1955; pp. 602-613.
Ravon, D. et al., "Monoclonal antibody F1 Binds to the Kringle Domain of Factor XII and Induces Enhanced Susceptibility for Cleavage by Kallikrein"; Blood; vol. 86, No. 11; Dec. 1, 1995; pp. 4134-4143.
Renne, T. et al.; "Defective thrombus formation in mice lacking factor XII"; J. Exp. Med.; vol. 202, No. 2; Jul. 18, 2005; pp. 271-281.
Rodriguez, E. et al.; "Activatable magnetic resonance imaging agents for myeloperoxidase sensing: mechanism of activation, stability and toxicity"; J. Am. Chem. Soc.; vol. 132, No. 1; Jan. 13, 2010; pp. 168-177.
Ronald, J.A. et al.; "Enzyme-Sensitive Magnetic Resonance Imaging Targeting Myeloperoxidase Identifies Active Inflammation in Experimental Rabbit Atherosclerotic Plaques"; Circulation; vol. 120; Aug. 3, 2009; pp. 592-599.
Schmaier, A.; "The elusive physiologic role of Factor XII"; J. Clin. Invest.; vol. 118, No. 9; Sep. 2008; pp. 3006-3009.
Tung, C.H. et al.; "Novel Factor XIII Probes for Blood Coagulation Imaging"; ChemBioChem. vol. 4; 2003; pp. 897-899.
Vermeer, S.E. et al.; "Silent Brain Infarcts and White Matter Lesions Increase Stroke Risk in the General Population: The Rotterdam Scan Study"; Stroke; vol. 34; Apr. 10, 2003; pp. 1126-1129.
Wen, L. et al.; "Nucleotide sequence of a cDNA clone that encodes the maize inhibitor of trypsin and activated Hageman factor"; Plant Molecular Biology; vol. 18; 1992; pp. 813-814.
Werle, M. et al.; "Strategies to improve plasma half life time of peptide and protein drugs"; Amino Acids; vol. 30; 2006; pp. 351-367.
Williams, A. et al.; "DX-88 and HAE: a developmental perspective"; Transfus. Apheresis Sci.; vol. 29; 2003; pp. 255-258.
International Search Report and Written Opinion dated Jul. 27, 2012; International Application No. PCT/EP2012/054142 filed Mar. 9, 2012; 20 pages.
European Search Report dated Sep. 22, 2011; European Application No. 11157555.1; 10 pages.
Extended European Search Report dated Jan. 26, 2012; European Application No. 11157555.1; 18 pages.
Sato et al., White Matter Activated Glial Cells Produce BDNF in a Stroke Model of Monkeys, Neuroscience Research; (2009) 65:71-78.
Hagedorn et al., "In Vivo antithrombotic effect of a novel coagulation factor XIIa inhibitor in murine arterial thrombosis and stroke," Hämostaseologie, 30(1): A98, p. 15-11 (2010).

(56) References Cited

OTHER PUBLICATIONS

Yamagami et al., "Antiplatelet therapy in carotid artery stenting," Japanese Journal of Thrombosis and Hemostasis, 20(6): 602-607 (2009).
Sakai et al., "Thromboembolic risks during cerebral angiography with low osmolar contrast media—ionic versus non-ionic contrast media," The Clinical Report, 25(9): 153-157 (1991).

* cited by examiner

Figure 1

```
     ###      #######      # ##                          # #
Rho  EGGEPC-----ACPHALHRVCGSDGETYSNPCTLNCAKFNGKPELVKVHDGPC
I4   EVRNPC-----ACFRNYVPVCGSDGKTYGNPCMLNCAAQTKVPGLKLVHEGRC
SP   GREAKCYNELNGCTKIYDPVCGTDGNTYPNECVL-CFENRKRTSILIQKSGPC
                ++++++++++++         ++   +      +
```

Figure 2

* denotes identical; | denotes similar amino acid; bold amino acids are conserved cysteines; underlined amino acids 2-13 of the Infestin-4 sequence are conserved.

```
             1   5        10   15   20   25   30   35   40   45
I4           EVRNPC-----ACFRNYVPVCGSDGKTYGNPCMLNCAAQTKVPGLKLV-HEGRC
             * | *     * | * ****|** ** * *|* *   | *     *|   * *
SP:     DSLGREAK--CYNELNGCTKIYDPVCGTDGNTYPNECVL-CFENRKRQTSILIQKSGPC
             1   5        10   15   20   25   30   35   40   45   50   55
```

Figure 3

* denotes identical; | similar amino acids with regard to the Infestin-4 sequence.
Underlined amino acids in I4 were used to replace SP amino acids. Underlined amino
acids in K2 and K3 are additional point mutations on the K1 sequence.

```
I4         EVRNPC-----ACFRNYVPVCGSDGKTYGNPCMLNCAAQTKVPGLKLV-HEGRC
SP: DSLGREAK--CYNELNGCTKIYDPVCGTDGNTYPNECVL-CFENRKRQTSILIQKSGPC
         *  |  *       *  | * ****|** ** * *|* *   | *    *|    * *
K1: DSLGREVRNPC-----ACFRNYVPVCGTDGNTYPNECVL-CFENRKRQTSILIQKSGPC
         ******       ***********|** ** * *|* *   | *    *|    * *
K2: DSLGREVRNPC-----ACFRNYVPVCGTDGNTYGNECML-CAENRKRQTSILIQKEGPC
         ******       ***********|** **** *** **  | *    *|   ** *
K3: DSLGREVRNPC-----ACFRNYVPVCGTDGNTYGNECMLNCAENRKRQTSILIQKEGPC
         ******       ***********|** **** ******  | *    *|   ** *
```

FACTOR XII INHIBITORS FOR THE TREATMENT OF SILENT BRAIN ISCHEMIA AND ISCHEMIA OF OTHER ORGANS

This application is the United States national stage of PCT/EP2012/054142, filed Mar. 9, 2012, (published as WO 2012/120124), and also claims priority to European Patent Application No. 11 157 555.1, filed Mar. 9, 2011, U.S. Provisional Application No. 61/457,360, filed Mar. 9, 2011, and U.S. Provisional Application No. 61/496,746, filed Jun. 14, 2011, all of which are incorporated herein by reference.

FIELD

This application relates to silent brain ischemia and ischemia of other organs, a method of administering a Factor XII inhibitor in a patient receiving a medical procedure, and animal models useful for studying silent brain ischemia and ischemia in other organs, and for evaluating potential therapies.

BACKGROUND

Silent brain ischemia (SBI) is a condition of small ischemic injuries in the brain that are a side effect of medical procedures, particularly vascular procedures and surgeries. Ischemia can also occur in other organs. Any foreign or endogenous material that is accidentally released into the arterial circulation during a medical procedure may result in SBI or ischemia of other organs, such as diffuse embolic ischemia. SBI is a heterogeneous syndrome, in which the exact source of an embolus may vary. For example, an embolus or microembolus that causes SBI, or ischemia of other organs, may be comprised of diverse substances including bubbles, oil, fat, cholesterol, coagulated blood and/or debris. Usually, the ischemic injury is diffuse. In SBI, an area of the brain is showered by microemboli and individual foci are difficult to detect with conventional magnetic resonance imaging (MRI). For example, microembolic signals are found during the injection of contrast agent and during probing of vessels (Bendszus M and Stoll G, 5 Lancet Neurol. 364-372, 2006). The exact mechanism of the tissue damage in SBI is unknown (Bendszus M and Stoll G, 5 Lancet Neurol. 364-372, 2006).

Due to the diffuse nature of the injury, a patient with SBI usually lacks focal, clearly defined neurological deficits as in stroke. However, behavioral changes, neuropsychological deficits and aggravated vascular dementia are frequently observed in a large number of patients after major surgery (e.g. coronary bypass, valve replacement surgery, carotid endarterectomy or stenting) and in many patients with vascular interventions, coronary angiography, arterial lines or intra-aortic counterpulsation devices in intensive care units. These symptoms are extremely common after medical procedures, but are rarely seen as directly related to the procedure. With the advent of increasingly sensitive imaging modalities such as diffusion-weighted MRI (DWI), there has been an increasing awareness of injuries to the brain that present without overt clinical symptoms such as paralysis or sensitivity defects.

Up to 45% of patients who have had surgeries and procedures develop SBI, especially those that involve the heart and vascular structures. Coronary angiography, performed over two million times annually in the USA, has a risk of SBI of 11-15% (Bendszus M and Stoll G, 5 Lancet Neurol. 364-372, 2006). Up to 26% of patients that underwent diagnostic angiography, up to 54% of patients that underwent carotid artery stenting and up to 45% of patients after heart surgery may be afflicted with SBI (Bendszus M and Stoll G, 5 Lancet Neurol. 364-372, 2006).

The clinical manifestations of SBI include behavioral and neuropsychological changes, in addition to increased risk for cognitive decline, increased risk of stroke and worsening dementia (Vermeer S E et al. 34 Stroke 1126-1129, 2003; Kobayashi S et al. 28 Stroke 1932-1939, 1997). The presence of SBI has been shown to more than double the risk of dementia in patients 60-90 years of age, and results in a steeper decline in global cognitive function and worse performance on neuropsychological testing (Vermeer S E et al. 34 Stroke 1126-1129, 2003; Lopez O L et al. 60 Arch. Neurol. 1394-1399, 2003).

SBI is distinct from clinical stroke. Clinical stroke leads to clearly defined neurological deficits, and often either involves the spontaneous rupture of a vulnerable plaque in an artery that supplies the brain with oxygenated blood or is due to thrombembolism from the heart caused by atrial fibrillation. In contrast to stroke, patients who are at risk for SBI may not have underlying atherosclerotic disease or risk factors for stroke or thrombosis. Patients that undergo a vascular procedure may include, for example, a patient with a congenital heart defect. Such patients, who are otherwise healthy, are still at risk for SBI as a side effect of the microemboli introduced during a medical procedure (Harrison's Principles of Internal Medicine 16$^{th}$ Ed. (Kasper D L, Fauci, A S, Longo, D L, Braunwald E, Hauser S L, Jameson J L eds., 2005)). Therefore the patient population that would benefit from a preventative therapy or treatment of SBI includes patients undergoing a medical procedure involving contact with structures of the vascular system.

Although heparin has been shown to reduce clinically silent embolic events caused by intra-arterial cerebral angiography (Bendszus et al., Circulation 110:2110-2115, 2004), it carries a relatively high risk of extra- and intracranial bleeding complications. Moreover, it is not clear if different SBI events, caused by different types of emboli, involve similar molecular mechanisms and/or would be treatable using similar therapeutics. A desired therapy would reduce ischemic injury caused by all types of emboli, including microemboli comprised of bubbles, oil, fat, cholesterol, coagulated blood and/or debris, but would not affect hemostasis such as heparin does. Accordingly, an effective and safe treatment for SBI and ischemia in other organs, such as diffuse embolic ischemia, irrespective of the cause, is needed. The development of an animal model to study SBI and evaluate treatments has been challenging, since diffuse micro-injuries need to be produced without causing overt stroke. Thus, realistic animal models of SBI are still needed to study the molecular mechanisms of tissue damage and to evaluate therapeutic candidates.

Factor XII (FXII) is a serine protease that is involved in the activation of the intrinsic coagulation cascade. Recently, it was found that deficiency or inhibition of Factor XII in mice reduced brain damage in stroke models and was protective against arterial thrombus formation, but without increasing the risk of bleeding (WO 2006/066878; WO 2008/098720; Kleinschnitz C et al. 203 J. Exp. Med. 513-518, 2006; Renne T et al. 202 J. Exp. Med. 271-281, 2005). Similar to FXII deficient mice, humans that are deficient in FXII do not suffer from abnormal bleeding diathesis, even during major surgical procedures (Ratnoff O D and Colopy J E, 34 J. Clin. Invest. 602-613, 1955; Colman R W, Hemostasis and Thrombosis. Basic Principles & Clinical Practice 103-122 (Colman R W, Hirsch J, Mader V J, Clowes A W, George J eds., Lippincott Williams & Wilkins, Philadelphia, 2001); Schmaier A H, 118 *J. Clin. Invest.* 3006-3009, 2008).

Recently, Infestin-4 was reported to be a novel inhibitor of activated FXII (FXIIa). Infestins are a class of serine protease inhibitors derived from the midgut of the hematophagous insect, *Triatoma infestans*, a major vector for the parasite *Trypanosoma cruzi*, known to cause Chagas' disease (Campos I T N et al. 32 *Insect Biochem. Mol. Bio.* 991-997, 2002; Campos I T N et al. 577 *FEBS Lett.* 512-516, 2004). This insect uses these inhibitors to prevent coagulation of ingested blood. The Infestin gene encodes 4 domains that result in proteins that can inhibit different factors in the coagulation pathway. In particular, domain 4 encodes a protein (Infestin-4) that is a strong inhibitor of FXIIa. Infestin-4 has been administered in mice without bleeding complications (WO 2008/098720).

Despite the heterogeneous mechanisms leading to SBI and ischemia in other organs, including diffuse embolic ischemia, the embodiments of this application provide inhibitors of FXII, particularly proteins comprising Infestin-4, and variants thereof, to treat SBI and ischemia in other organs. Further, the application provides animal models of SBI that mimic various types of emboli that may enter into the circulation during a medical procedure. The animal models described herein may be useful as tools to study SBI and evaluate therapeutic candidates.

SUMMARY

The application provides a method of administering a Factor XII (FXII) inhibitor in a patient receiving a medical procedure, wherein the medical procedure comprises contact with at least one of: heart; at least one blood vessel chosen from: the aorta, the aortic arch, a carotid artery, a coronary artery, brachiocephalic artery, vertebrobasilar circulation, intracranial arteries, renal artery, a hepatic artery, a mesenteric artery, and/or a blood vessel of the arterial system cranial to the heart; and a venous blood vessel if the patient has a known septal defect. The medical procedure comprises release of at least one embolus in at least one of said blood vessels in the body that could result in ischemia of a target organ, and administration of the FXII inhibitor before, during, and/or after the medical procedure. A "FXII inhibitor" refers to inhibitors of either or both of Factor XII and activated Factor XII (FXIIa).

An embolus may be comprised of various materials. For example, an embolus is comprised of bubbles, oil, fat, cholesterol, coagulated blood, and/or debris. In one embodiment, the embolus is not a thrombus.

In one embodiment, the target organ is the brain, and the patient has, has had, or is at risk for (i) silent brain ischemia, or (ii) a stroke caused by a nonthrombolysable substance. In another embodiment, the target organ is the heart, kidney, liver, and/or gastrointestinal tract organ, including the esophagus, stomach, small intestine, and/or large intestine (including colon and/or rectum).

In one embodiment, the medical procedure comprises contact with the inside of at least one of said blood vessels. In another embodiment, the medical procedure comprises clamping of one or more of said blood vessels.

In one embodiment, the medical procedure is a vascular surgery. In certain embodiments, the medical procedure is coronary angiography, carotid artery stenting, percutaneous coronary intervention, carotid endarterectomy, or a cardiovascular surgery. In another embodiment, the medical procedure is dilation of the stenotic renal artery. In one embodiment, the medical procedure is a vascular procedure that is diagnostic. In certain embodiments, the medical procedure is a vascular procedure that comprises any one or more of a catheter, a stent, a balloon, and/or a graft. In another embodiment, the medical procedure comprises administering a contrast agent, as, amongst others, the injection of a contrast agent can inadvertently create air bubbles and/or dislodge debris.

In one embodiment, the FXII inhibitor comprises the wild type Infestin-4 (SEQ ID NO: 1) polypeptide sequence, or a variant thereof. In another embodiment, a variant of Infestin-4 comprises the N-terminal amino acids 2-13 of the wild type Infestin-4 sequence, and at least one and up to five amino acid mutations outside said N-terminal amino acids that result in differences from the wild type Infestin-4 sequence, and/or comprises six conserved cysteine residues and homology of at least 70% to the wild type Infestin-4 sequence. See FIG. 2. In another embodiment, the FXII inhibitor comprises SPINK-1 (SEQ ID NO: 2), a human protein expressed in the pancreas, which is mutated to include the N-terminal amino acids 2-13 of the wild type Infestin-4 sequence, given as SEQ ID NO: 3, or a variant of said mutated SPINK-1. In certain embodiments, a variant of said mutated SPINK-1 comprises the N-terminal amino acids 2-13 of the wild type Infestin-4 sequence, and has at least one and up to five amino acid mutations outside said N-terminal amino acids that result in differences from the wild type SPINK-1 sequence and which increase the homology of the variant to the wild type Infestin-4 sequence, and/or comprises six conserved cysteine residues and homology of at least 70% to the wild type SPINK-1 sequence. In one embodiment, the FXII inhibitor is SPINK K1, K2, or K3 (SEQ ID NO: 3, 4 or 5).

In another embodiment, the FXII inhibitor is chosen from AT III inhibitor, angiotensin converting enzyme inhibitor, C1 inhibitor, aprotinin, alpha-1 protease inhibitor, antipain ([(S)-1Carboxy-2-Phenylethyl]-Carbamoyl-L-Arg-L-Val-Arginal), Z-Pro-Pro-aldehyde-dimethyl acetate, DX88, leupeptin, inhibitors of prolyl oligopeptidase such as Fmoc-Ala-Pyr-CN, corn-trypsin inhibitor, mutants of the bovine pancreatic trypsin inhibitor, ecotin, YAP (yellowfin sole anticoagulant protein), *Cucurbita maxima* trypsin inhibitor-V and/or *Curcurbita maxima* isoinhibitors.

In yet another embodiment, the FXII inhibitor is an anti-FXII antibody. An anti-FXII antibody refers to an antibody that binds to and inhibits FXII and/or FXIIa.

In certain embodiments, the FXII inhibitor is linked to a half-life enhancing polypeptide (HLEP). In one embodiment, the HLEP may be, for example, albumin, afamin, alpha-fetoprotein or vitamin-D binding protein. In one embodiment, the HLEP may be human albumin or a variant thereof. In other embodiments, the HLEP is an immunoglobulin. The immunoglobulin portion may be an Fc from an IgG.

In another embodiment, the FXII inhibitor is linked to an HLEP via a linker. In one embodiment, the linker may be cleavable. In certain embodiments, the linker is cleaved by a coagulation protease of the intrinsic, extrinsic, and/or common coagulation pathway. In one embodiment, the linker is cleaved by FXIIa.

Another aspect of the application pertains to an animal model of SBI comprising a procedure, wherein the procedure comprises release of at least one embolus into the arterial system of an animal that could result in an ischemic injury in the brain, and evaluating the animal for an indication of an ischemic injury in the brain. The ischemic injury is clinically silent. The term "release" or "releasing" in this context encompasses both providing an external source of an embolus into the arterial system of the animal and using techniques to generate an embolus internally, but do not encompass inserting a thread into a blood vessel to generate a thrombus. In one embodiment, the procedure comprises releasing the embolus into the arterial system. In one embodiment, the procedure comprises releasing the embolus into the carotid artery. In certain embodiments, the procedure comprises releasing the embolus using a catheter. In another embodiment, the procedure comprises clamping and/or surgery. In one embodiment, the animal model comprises evaluating the animal for ischemic injury in other target organs, including the heart and/or kidney. In one embodiment, the procedure does not include inserting a thread into a blood vessel to generate a thrombus. In one embodiment, the procedure does not cause a stroke in the animal.

In one embodiment, the embolus comprises a fluorescent material. In certain embodiments, the embolus is comprised of a nonthrombolysable material (meaning that the embolus may not be lysed using a thrombolytic agent). In such embodiments, the embolus is not a thrombus. For example, the embolus may be comprised of a polymer, bubbles, oil, fat, cholesterol, and/or debris. In one embodiment, the embolus is a microbead (including a microsphere or microparticle). An embolus may be composed of 50%, 60%, 70%, 80%, 90%, 95%, 96%, 97%, 98%, 99%, or 100% of nonthrombolysable substance(s). In another embodiment, the embolus is comprised of coagulated blood. In embodiments, the evaluation comprises imaging and/or histology. In one embodiment, the imaging comprises MRI and/or SPECT. In one embodiment, the animal model is a mouse. In another embodiment, the animal model is a rat.

In another embodiment, the animal model is for evaluating a therapeutic candidate to reduce SBI. In this embodiment, a therapeutic is administered to an animal and is tested for its ability to reduce an ischemic injury in the brain. In another embodiment, the therapeutic is administered to an animal and tested for its ability to reduce ischemic injury in other target organs, including diffuse embolic ischemia. In certain embodiments, the therapeutic candidate is an inhibitor of the coagulation pathway. In one embodiment, the therapeutic is an inhibitor of FXII. In one embodiment, the therapeutic is an antibody. In another embodiment, the therapeutic is a protein, peptide, nucleic acid, or small molecule. In embodiments, the therapeutic candidate is administered to the animal before, during, and/or after the procedure.

In one embodiment, the imaging method, comprising MRI and/or SPECT imaging, is used to evaluate an ischemic injury in a target organ for the development of inhibitors of FXII. The imaging method is performed before and/or after administration of an inhibitor of FXII. In one embodiment, the target organ is the brain.

Additional embodiments are set forth in the items that follow.

Item 1. Inhibitor of Factor XII (FXII) for use in the prevention and/or treatment of ischemia in a patient receiving a medical procedure, wherein the medical procedure comprises contact with at least one of:
(a) heart,
(b) at least one blood vessel chosen from: the aorta, the aortic arch, a carotid artery, a coronary artery, brachiocephalic artery, vertebrobasilar circulation, intracranial arteries, renal artery, a hepatic artery, a mesenteric artery, and/or a blood vessel of the arterial system proximal to the heart,
(c) a venous blood vessel if the patient has a known septal defect;
and wherein the medical procedure comprises release of at least one embolus in at least one of said blood vessels in the body that could result in said ischemia in at least one target organ and wherein the FXII inhibitor is administered before, during, and/or after the medical procedure.

Item 2. Inhibitor of Factor XII for use according to item 1, wherein the embolus is comprised of bubbles, oil, fat, cholesterol, coagulated blood, and/or debris.

Item 3. Inhibitor of Factor XII for use according to items 1 and 2, wherein the target organ is:
(a) brain, and wherein the patient has, has had, or is at risk for silent brain ischemia or a stroke, wherein the stroke is caused by a nonthrombolysable substance; and/or
(b) heart, kidney, liver; and/or gastrointestinal tract organ.

Item 4. Inhibitor of Factor XII for use according to items 1 to 3, wherein the medical procedure comprises:
(i) contact with the inside of at least one or more of said blood vessels;
(ii) clamping of at least one of more of said blood vessels;
(iii) a vascular procedure that comprises any one or more of a catheter, a stent, a balloon, a graft, and/or administering a contrast agent;
(iv) a vascular surgery and/or is a vascular procedure that is diagnostic; and/or
(v) coronary angiography, carotid artery stenting, percutaneous coronary intervention, carotid endarerectomy, a cardiovascular surgery, or dilation of stenotic renal artery.

Item 5. Inhibitor of Factor XII for use according to items 1 to 4, wherein the FXII inhibitor comprises:
(i) the wild type Infestin-4 polypeptide sequence (SEQ ID NO: 1), or a variant thereof, wherein a variant comprises
　(a) the N-terminal amino acids 2-13 of the wild type Infestin-4 sequence and at least one and up to five amino acid mutations outside said N-terminal amino acids that result in differences from the wild type Infestin-4 sequence; and/or
　(b) six conserved cysteine residues and homology of at least 70% to the wild type Infestin-4 sequence;
(ii) SPINK-1, which is mutated to include the N-terminal amino acids 2-13 of the wild type Infestin-4 sequence, or a variant of said mutated SPINK-1, wherein a variant comprises
　(a) the N-terminal amino acids 2-13 of the wild type Infestin-4 sequence and at least one and up to five amino acid mutations outside said N-terminal amino acids that result in differences from the wild type SPINK-1 sequence and which increase the homology of the variant to the wild type Infestin-4 sequence; and/or
　(b) six conserved cysteine residues and homology of at least 70% to the wild type SPINK-1 sequence;
(iii) AT III inhibitor, angiotensin converting enzyme inhibitor, C1 inhibitor, aprotinin, alpha-1 protease inhibitor, antipain ([(S)-1-Carboxy-2-Phenylethyl]-Carbamoyl-L-Arg-L-Val-Arginal), Z-Pro-Pro-aldehyde-dimethyl acetate, DX88, leupeptin, inhibitors of prolyl oligopeptidase such as Fmoc-Ala-Pyr-CN, corn-trypsin inhibitor, mutants of the bovine pancreatic trypsin inhibitor, ecotin, YAP (yellowfin sole anticoagulant protein), *Cucurbita maxima* trypsin inhibitor-V, *Curcurbita maxima* isoinhibitors and/or Pro-Phe-Arg-chloromethyl-ketone (PCK); and/or
(iv) anti-FXII antibody, wherein the antibody binds to FXII and inhibits its activity and/or activation.

Item 6. Inhibitor of Factor XII for use according to item 5, wherein the variant of the mutated SPINK-1 is SPINK K1, K2, or K3 (SEQ ID NO: 3, 4, or 5).

Item 7. Inhibitor of Factor XII for use according to item 1 to 5, wherein the FXII inhibitor is linked to a half-life enhancing polypeptide, wherein the half-life enhancing polypeptide is optionally:
(i) albumin, afamin, alpha-fetoprotein or vitamin D binding protein; or
(ii) human albumin or a variant thereof; or
(iii) an immunoglobulin or a variant thereof; or
(iv) an Fc of an IgG.

Item 8. Inhibitor of Factor XII for use according to item 7, wherein the half-life enhancing polypeptide is linked to the FXII inhibitor via a linker and wherein the linker is optionally cleavable by a coagulation protease of the intrinsic, extrinsic, or common coagulation pathway.

Item 9. Use of an imaging method for the development of inhibitors of Factor XII comprising administering a Factor XII inhibitor candidate and evaluating the effect of the Factor XII inhibitor candidate on an ischemia in a target organ of an animal using radiology or nuclear medicine, e.g. CT (optionally SPECT-CT and/or FMT-CT); MRI (optionally diffusion-weighted MRI (DWI) and/or fMRI); PET; optical imaging (optionally fluorescence reflectance imaging; ultrasound, microscopy, fluoroscopy, autoradiography, and/or phosphor imaging), wherein the ischemia is caused by an embolus, and
(i) the target organ is brain, heart, kidney, liver, and/or gastrointestinal tract organ and
(ii) if the target organ is the brain, further wherein the ischemic injury is clinically silent and/or the embolus is nonthrombolysable.

Item 10. Use of a histology method for the development of inhibitors of Factor XII comprising administering a Factor XII inhibitor candidate and evaluating the effect of the Factor XII inhibitor candidate on an ischemia in a target organ of an animal using TTC staining, immunohistochemistry and/or histochemistry, wherein the ischemia is caused by an embolus, and
(i) the target organ is brain, heart, kidney, liver, and/or gastrointestinal tract organ and
(ii) if the target organ is the brain, further wherein the ischemic injury is clinically silent and/or the embolus is nonthrombolysable.

Item 11. An animal model of ischemia comprising
(a) a procedure, wherein the procedure comprises intentionally releasing at least one embolus in the arterial system that could result in an ischemic injury in at least one target organ,
   (i) wherein the target organ is brain, heart, kidney, liver, and/or gastrointestinal tract organ; and
   (ii) if the target organ is the brain, further wherein the ischemic injury is clinically silent and/or the embolus is nonthrombolysable; and
(b) evaluating the animal for an indication of an ischemic injury in the target organ.

Item 12. The method according to item 9 to 11, wherein the procedure comprises
(i) releasing the embolus into a blood vessel;
(ii) releasing the embolus into an artery.
(iii) releasing the embolus into heart, aorta, aortic arch, a carotid artery, a coronary artery, brachiocephalic artery, vertebrobasilar circulation, intracranial arteries, renal artery, a hepatic artery, a mesenteric artery, and/or a blood vessel of arterial system cranial to heart; and/or
(iv) releasing the embolus into a carotid artery.

Item 13. The method according to items 9 or 11, wherein the evaluation step comprises magnetic resonance imaging, and/or SPECT imaging.

Item 14. The method according to items 9 to 11, for evaluating a therapeutic candidate to treat ischemia, wherein
(i) the therapeutic candidate is tested for its ability to reduce an ischemic injury in the target organ, and wherein the therapeutic candidate is administered to the animal before, during, and/or after the procedure; and/or
(ii) the therapeutic candidate is an inhibitor of the coagulation pathway.

Item 15. The method according to items 9 to 14, wherein the therapeutic candidate is
(i) a FXII inhibitor or
(ii) an antibody or
(iii) a small molecule.

Additional objects and advantages of the embodiments in the application appear in part in the following description and in part will be obvious from the description, or they may be learned in practice. The objects and advantages of the embodiments will manifest themselves by means of the elements and combinations particularly pointed out in the appended claims.

DESCRIPTION OF THE DRAWINGS

The patent or application file contains at least one drawing executed in color. Copies of this patent or patent application with color drawings will be provided by the Office upon request and payment of the necessary fee.

FIG. 1. Contact sites of *R. prolixus* inhibitor with thrombin and of SPINK-1 with chymotrypsin. # denotes amino acids that are contact sites between *R. prolixus* inhibitor and thrombin; + denotes amino acids that are contact sites between SPINK-1 and chymotrypsin. Amino acid sequences of Infestin-4 (I4: SEQ ID NO: 1), *R. prolixus* inhibitor (Rho: SEQ ID NO: 10), and SPINK-1 (SP: SEQ ID NO: 2) are aligned.

FIG. 2. Amino acid sequence similarity between Infestin-4 (I4; SEQ ID NO: 1) and SPINK-1 (SP: SEQ ID NO: 2). *denotes identical amino acid; | denotes similar amino acid; bold amino acids are conserved cysteines; underlined amino acids 2-13 of the Infestin-4 sequence are conserved.

FIG. 3. Amino acid sequences of Infestin-4 (I4: SEQ ID NO: 1), SPINK1 (SP: SEQ ID NO: 2) and three SPINK1 variants (K1, K2, and K3) (SEQ ID NOs: 3, 4, or 5). * denotes identical; | denotes similar amino acids with regard to the Infestin-4 sequence. The underlined sequence of 14 was used to replace 15 amino acids of SPINK-1 to generate K1. Variants K2 and K3 were generated by additional point mutations (amino acids underlined) on the K1 sequence.

DETAILED DESCRIPTION

Figure 4:
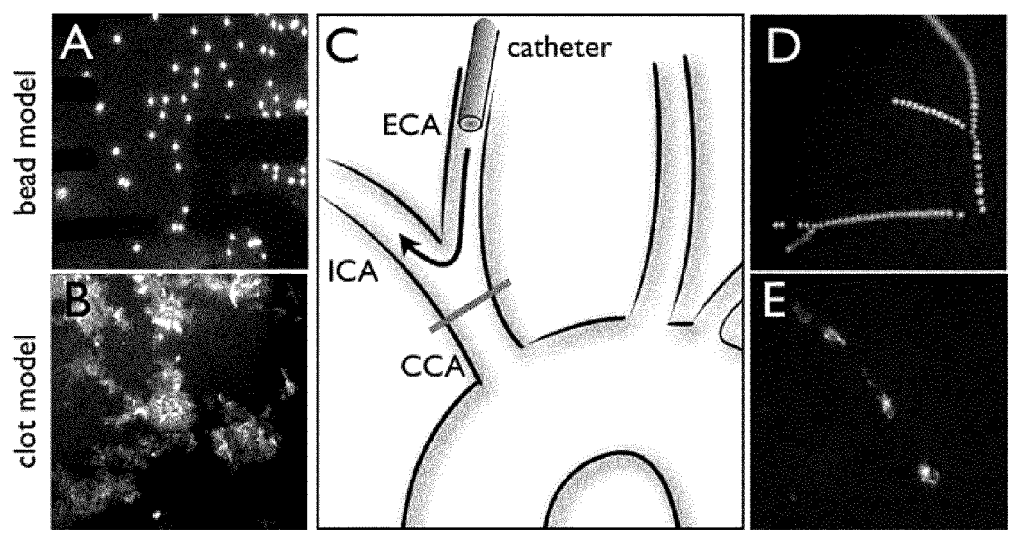
FIG. 4. Model. (A) Fluorescence image of FTC+ microbeads prior to injection. (B) Fluorescence image of ex vivo formed and labeled coagulated blood made from fresh mouse blood. (C) Cartoon that illustrates administration of emboli. The delivery catheter is inserted into the external carotid artery (ECA). ICA: Internal carotid artery, CCA: Common carotid artery. During injection, the CCA is temporarily ligated to force emboli into the ICA. (D, E) Fluorescence images of the brain surface after injection of either microbeads (D) or coagulated blood (E).

The embodiments of the application pertain to a method of administering a Factor XII (FXII) inhibitor in a patient receiving a medical procedure, wherein the medical procedure comprises contact with at least one of: heart; at least one blood vessel chosen from: the aorta, the aortic arch, a carotid artery, a coronary artery, brachiocephalic artery, vertebrobasilar circulation, intracranial arteries, renal artery, a hepatic artery, a mesenteric artery, and/or a blood vessel of the arterial system cranial to the heart; and a venous blood vessel if the patient has a known septal defect. The medical procedure comprises release of at least one embolus in at least one of said blood vessels in the body that could result in ischemia of a target organ, and administration of the FXII inhibitor before, during, and/or after the medical procedure. The ischemia may be caused by various types of emboli, irrespective of whether the embolus is comprised of bubbles, oil, fat, cholesterol, coagulated blood and/or debris. In one embodiment, the target organ is the brain, and the patient has, has had, or is at risk for SBI. Further, the embodiments of the application provide animal models of SBI that may be useful for the study of SBI and for the evaluation of therapeutic candidates.

One advantage of the embodiments of the application is that SBI may be reduced in patients having an array of medical procedures or presenting with or without different disease conditions. The success of the claimed method is not dependent on whether a patient has or does not have any of the following procedures or disease conditions. The success of the claimed method is therefore not dependent on whether the patient has or does not have any underlying diseases or, for example, an underlying risk of thrombosis. In fact, the claimed method is believed to function effectively in patients without an underlying risk of thrombosis for example, but who are receiving a medical procedure, for example, to correct a congenital heart defect. Therefore, the patient population is broader than, and thus distinct from, the patient population that is at risk for thrombosis. The application intends to claim patient population subsets including or excluding those having certain procedures or disease conditions.

I. DEFINITIONS

The abbreviation "FXII", as used in this application, refers to either or both of Factor XII and activated Factor XII (FXIIa). Thus, the term "FXII inhibitor" includes inhibitors of either or both of FXII and FXIIa. Further, anti-FXII antibodies includes antibodies that bind to and inhibit either or both of FXII and FXIIa.

As used here, the term "ischemia" refers to the condition in a human patient, or in an animal, of insufficient blood supply to a tissue or target organ which would result in ischemic injury, if not treated. For instance, cerebral or "brain ischemia" refers to a reduction in blood to the brain, such that the oxygen supply does not meet the demand of the brain tissue. A brain "infarct" refers to dead brain tissue that can result if ischemia or the cessation of blood flow lasts long enough to result in cell death. Infarcts may be characterized using computed tomography (CT) or MRI. Infarcts may also refer to dead tissue caused by small ischemic injuries or microlesions that are characterized as diffuse and too small to result in clear changes on conventional MRI. Such small infarcts may be visible with more sensitive imaging modalities, such as diffusion weighted MRI.

The term "ischemic injury" as used herein, refers to a spectrum of damage that may occur to a target organ as a result of ischemia, such as diffuse or focal ischemia, micro-injuries, transitory ischemia, micro-lesions, lesions, micro-infarcts or infarcts. Ischemic injuries may be further characterized in that they can be caused by an embolus comprising bubbles, oil, fat, cholesterol, coagulated blood, and/or debris. Depending on the size of the embolus, different events may result. For example, if the embolus, such as a nonthrombolysable substance (including an air bubble), is larger, it could cause a stroke. Such an event could be a side effect of heart surgery or an intraarterial procedure. If the embolus, such as an air bubble, is smaller or there is a plurality of small emboli, such as a plurality of air bubbles, it could cause an SBI. In one embodiment, stroke, for example, is caused by an embolus comprised of an air bubble.

The term "silent", when referring to "silent brain ischemia" ("SBI"), or a "silent brain infarct", or "clinically silent", refers to a condition of ischemia in brain tissue that lacks acute and overt stroke-defining symptoms, such as hemiparesis, hypesthesia, and/or aphasia, for example. Stroke may be defined as any acute clinical event related to impairment of cerebral circulation resulting in a focal neurological deficit that lasts for more than 24 hrs. SBI may be associated with more subtle neurological deficits, including, but not limited to, behavioral changes, worse cognitive ability, visual field deficits, arm and leg disturbances, frailty, depressive symptoms, decline in physical function, and aggravated vascular dementia. For example, infarcts that relate to prior transient ischemic attack or stroke-like symptoms may be defined as symptomatic, whereas those without corresponding stroke-like symptoms may be defined as "silent". The term "silent" does not mean that there are no symptoms; it means that the symptoms are distinct from typical stroke and generally more subtle, and in certain instances only manifest themselves in other ways, which could only be detected by sophisticated imaging or more intense testing such as cognitive testing. The term "diffuse", when referring to diffuse embolic ischemia in an organ, refers to a characteristic of the ischemia, which is caused by a scattering of emboli to more than one location in the organ, i.e. the ischemia is not focal.

As used here, the term "reducing" comprises lowering the likelihood of an SBI in an individual or in an animal, lowering the severity of any symptoms, and/or lowering the proportion of patients in a population at risk for SBI that actually have an SBI. Thus, "reducing" refers to decreasing, lowering, lessening, limiting, ameliorating, or improving a condition of SBI. Reducing SBI may include, for example, protecting against the occurrence of SBI; reducing the risk of SBI, reducing the severity of SBI as it develops, or once it has developed; limiting the damage of an SBI, e.g. limiting an ischemic injury from developing into an infarct; reducing the spread of SBI, e.g. limiting the amount of brain area or blood vessels that are affected or damaged by an ischemic injury; or improving conditions in the brain associated with an SBI, such as inflammation or edema.

In one embodiment, the patient has or has had SBI. In certain embodiments the patient is "at risk" for SBI. A patient that is "at risk" for SBI, includes a patient that has received, is receiving, or will receive a medical procedure comprising contact with any one of: heart; aorta, aortic arch, a carotid artery, a coronary artery, brachiocephalic artery, vertebrobasilar circulation, intracranial arteries, renal artery, a hepatic artery, a mesenteric artery, and/or a blood vessel of the arterial system cranial to the heart; and a venous blood vessel if the patient has a known septal defect. A patient "at risk" for SBI has received, is receiving, or will receive a medical procedure comprising release of at least one embolus in a blood vessel in the body. A method of administering a FXII inhibitor to a patient that has, has had, or is "at risk" for SBI may occur before, during and/or after the medical procedure to limit the occurrence of an SBI, or to limit the development or ameliorate the damage of an SBI. In certain embodiments, the patient need not have an SBI to be administered the FXII inhibitor. For example, a patient may not have an SBI prior to the medical procedure, or it may be unknown if the patient has an SBI before, during, and/or after the medical procedure, but in these cases, the patient is "at risk" of an SBI due to the medical procedure, and thus may be administered the FXII inhibitor. In certain embodiments, the patient or animal may have an SBI before, during, and/or after administration of the FXII inhibitor. In certain embodiments, the patient or animal may not have an SBI before, during, and/or after administration of the FXII inhibitor.

The term, "could result" is meant to include the scenario wherein ischemia to a target organ occurs in a patient or animal that receives a procedure that generates an embolus and the patient or animal has not yet received the FXII inhibitor; it also includes the scenario wherein ischemia to a target organ does not occur in a patient or animal that receives a procedure because the patient or animal has previously or concurrently received administration of the FXII inhibitor. The ischemia (and any infarct that would have occurred if the ischemia continued) may also not occur if the patient or animal receives the FXII inhibitor within a short time after the procedure, such as within 1, 2, 3, 4, 5, 6, 7, 8, 9, 10, 15, 20, or 30 minutes, within 1 hour, or within 2, 4, 6, 8, 12, 24, 28, 72, or 96 hours of the conclusion of the procedure.

For example, in one embodiment of the animal model, the FXII inhibitor may be administered before, during, and/or shortly (as defined above) after the procedure, and thus, the animal may not develop an SBI. In another embodiment of the animal model, the FXII inhibitor may be administered after the procedure, and the animal may develop an SBI. This term also refers to the fact that not each and every patient who has one of the encompassed medical procedures will, in fact, have an embolus dislodged. Each of these scenarios is included in the embodiments of this application.

The phrase "inducing silent brain ischemia" in an animal subject refers to the method wherein said animal has an indication of an ischemic injury, such as an infarct in the brain, for example, by imaging and/or histology, and wherein the symptoms are clinically silent, as described above and in Example 2A.

A patient "receiving" a medical procedure refers to a patient that is going to have a medical procedure, is having a medical procedure, or has had a medical procedure.

The term "allowing" as used in "allowing the FXII inhibitor to reduce an ischemic injury" is defined as administering a FXII inhibitor in an amount and via a route of administration that is sufficient to reduce an ischemic injury in the brain. The terms "reduce" and "ischemic injury" are defined above. The amount of ischemic injury may be assessed by various imaging modalities, which include but are not limited to MRI and/or CT.

"Embolus" refers to any detached intravascular matter comprised of a solid, liquid, or gas that is capable of occluding a vessel. The occlusion can occur at a site distant from the point of origin. The composition of an embolus includes, but is not limited to, bubbles or $CO_2$; oil, fat, cholesterol; debris, such as vessel debris, e.g. calcifications, tissue, or tumor fragments; coagulated blood, an organism such as bacteria or a parasite, or other infective agent; or foreign material. The term "bubbles" includes an embolus formed of air or other gas, or in certain instances, a liquid that is not blood or coagulated blood. A bubble may be spherical or non-spherical in shape. In one embodiment, the embolus is not a thrombus. In another embodiment, an embolus is comprised of coagulated blood. The term "microembolus" is included in the term "embolus" as used herein, and refers to an embolus of microscopic size and may be comprised of the same materials as an embolus as defined above. Thus an "embolus" includes singular or plural emboli, microemboli, showers of emboli, or showers of microemboli.

An embolus may be an arterial embolus, where the detached intravascular matter is in an artery or vessel of the arterial system. In one embodiment, an embolus is a "paradoxical embolus", which refers to an embolus of venous origin that passes into the arterial system, such as due to a septal defect.

"Homology" refers to the percentage number of amino acids that are identical or constitute conservative substitutions. Homology may be determined using sequence comparison programs such as GAP (Deveraux et al., 1984, Nucleic Acids Research 12, 387-395), which is incorporated herein by reference. In this way sequences of a similar or substantially different length to those cited herein could be compared by insertion of gaps into the alignment, such gaps being determined, for example, by the comparison algorithm used by GAP.

II. MEDICAL PROCEDURES

In one embodiment, a FXII inhibitor is administered to a patient receiving a medical procedure. As used herein, the term "medical procedure" refers to an act of diagnosis, intervention, treatment, or surgery. In one embodiment, the medical procedure comprises contact with at least one of: heart; at least one blood vessel chosen from: the aorta, the aortic arch, a carotid artery, a coronary artery, the brachiocephalic artery, vertebrobasilar circulation, intracranial arteries, renal artery, a hepatic artery, a mesenteric artery, and/or a blood vessel of the arterial system cranial to the heart; a venous blood vessel if the patient has a known septal defect. As used herein, the term "contact" refers to the physical touching of said vascular structures by an instrument, external object, person e.g. a surgeon, or any other object that touches said vascular structure due to the medical procedure. In one embodiment, the medical procedure comprises contact with the inside of at least one of said blood vessels. In certain embodiments, the medical procedure comprises clamping of one or more of said blood vessels. In embodiments, the medical procedure includes release of an embolus and the embolus may be comprised of bubbles, oil, fat, cholesterol, coagulated blood, and/or debris. In embodiments, the medical procedure comprises any or more of a catheter, a stent, a balloon, a graft, and/or administering a contrast agent, as, amongst others, the injection of a contrast agent can inadvertently create air bubbles and/or dislodge debris.

In one embodiment, the medical procedure is a vascular procedure. The term "vascular procedure" encompasses any procedure affecting the heart or a blood vessel, wherein a vessel is defined as a structure conveying or containing blood. Vascular procedures may involve for example, using a catheter or administering a contrast agent. In certain embodiments, the medical procedure involves the arterial system, referring to a procedure that involves an artery, arterial branches, arterioles, capillaries, or vessels involved in conveying blood away from the heart. In embodiments, the medical procedure involves one or more of the following vessels: the aorta, the aortic arch, a carotid artery, a coronary artery, brachiocephalic artery, vertebrobasilar circulation, intracranial arteries, renal artery; a hepatic artery, including for example, the common hepatic artery and/or the hepatic artery proper; a mesenteric artery, including for example, the superior mesenteric artery, and/or the inferior mesenteric artery; and/or a blood vessel of the arterial system cranial to the heart; a venous blood vessel if the patient has a known septal defect.

The term "diagnostic" refers to a procedure that is performed to identify or evaluate a condition, disease, or disorder. A diagnostic procedure may involve for example, using any one or more of a catheter, stent, balloon, graft and/or administering a contrast agent.

In one embodiment, the medical procedure is a vascular surgery. A vascular surgery refers to an operation involving a vascular structure, such as the heart or a blood vessel. Examples of vascular surgeries include, but are not limited to, cardiovascular surgery, e.g. coronary-artery bypass graft; or cardiac artery graft without cardiopulmonary bypass; cardiac valve replacement or repair, including for example, aortic or mitral valve, aortic, or mitral valvotomy or valvuloplasty; cardiac transplant; operation to improve a condition of stenosis or regurgitation; operation involving pacemakers, including temporary or permanent pacemaker, bi-ventricular pacemaker; operation involving generator change, lead extraction or implantable loop recorder, implanted cardioverter/defibrillator device, or mechanical device to support circulation, e.g. extracorporeal pump or ventricular assist device; carotid endarterectomy; thromboendarterectomy; aortic aneurysm and dissection surgery; dialysis access procedure such as arterial-venous fistulas; surgery involving cardiac tumor or traumatic cardiac injury; and reconstructive surgery or any other currently known or future vascular surgery.

A vascular surgery may for example involve a corrective operation for a congenital heart defect. Corrective surgeries for congenital heart defects include, but are not limited to, operation to repair a malformation or defect, e.g. repair of an atrial or ventricular septal defect; repair of a patent ductus arteriosus; repair of a shunt; aortic coarctation repair; repair of total or partial anomalous pulmonary venous return; venous switch correction of complete transposition of the great arteries or intraventricular surgery; repair of tetralogy of Fallot; or any other currently known or future surgery for a congenital heart defect.

In one embodiment, the medical procedure comprises using a catheter. As used herein, the term "catheter" refers to a tube that is inserted into a blood vessel. Examples of procedures that involve using a catheter include, but are not limited to, stenting a vessel, such as a coronary artery, carotid artery stenting, intracranial stenting, aorta or iliac artery; angioplasty, such as balloon angioplasty; thrombectomy; catheter-directed thrombolysis; embolization, direct or local administration of chemotherapy or heat; cardiac valve replacement or repair; or aortic or mitral valvotomy or valvuloplasty. In one embodiment, the medical procedure involves any use of a catheter or a stent or a procedure involving vessel dissection or clamping. A vascular procedure may involve vessel probing, such as endovascular-coil occlusion, endovascular-aneurysm occlusion or intracranial vessel probing with application of foreign bodies (e.g. platinum coils).

In one embodiment, a medical procedure comprises imaging. Imaging may be used to visualize biological and cellular processes in vivo, and may be used for screening, diagnosis, evaluation, monitoring or treatment of a condition, disease or disorder. Imaging may or may not involve using a catheter. Imaging techniques may image the vascular system, such as coronary angiography, including diagnostic angiography or catheter-based angiography, including looking at coronary vasculature, pulmonary vasculature, or vasculature of any part of the body, or aortogram.

In one embodiment, the medical procedure comprises administration of a contrast agent, radioisotope or dye. For a discussion of imaging modalities and commonly used contrast agents, see Pysz M A et al. 65 *Clinical Radiology* 500-516, 2010; examples of contrast agents and various imaging techniques are given below.

For example, contrast agents used in CT include, but are not limited to, barium, iodine, krypton, and xenon. Contrast agents used in single photon-emission computed tomography (SPECT-CT) include, but are not limited to, $^{99m}$Tc, $^{123}$I, $^{111}$In, $^{177}$Lu. Common contrast agents used in positron emission tomography (PET) include, but are not limited to isotopes, $^{11}$C, $^{18}$F, $^{64}$Cu, $^{68}$Ga. Contrast agents used in MRI include, but are not limited to, gadolinium ($Gd^{3+}$), iron oxide particles (SPIO, USPIO), manganese oxide, and $^{19}$F. Contrast agents used in magnetic resonance spectroscopy (MRS)

include, but are not limited to, choline, creatine, lactate, lipids, polyamines, and N-acetyl-aspartate. Contrast microbubbles may be used in ultrasound (US), such as, gas-filled microspheres (e.g. perfluorobutane) or lipid-shelled bubbles. Fluorescent molecules, dyes, and/or light absorbing particles may be used in optical imaging techniques. Radiotracers may be used in oncological, cardiovascular or neurological imaging, such as $^{11}$C, $^{18}$F, $^{64}$Cu, $^{111}$In, $^{99m}$Tc, $^{99}$Y, $^{131}$I, $^{123}$I-/$^{131}$I, and $^{153}$Sm. Capthesin B- or MMP2/9-activated "smart" fluorescent probes may be used in optical tomography. Contrast agents including NIRF dyes, quantum dots, and nanoparticles with surface enhanced Raman scattering (SERS) properties may be used in Raman spectroscopy. Other imaging techniques may include echocardiography (ECHO) with contrast such as microbubbles, including two-dimensional ECHO, stress echo, Doppler ECHO, and transoesophageal ECHO. Imaging techniques may include microscopy, photoacoustic imaging, or any other currently known or future molecular imaging modalities and/or associated contrast agents. Molecular imaging may involve administration of microbeads (including microspheres and microparticles) and nanoparticles that are bound to a tissue or disease specific marker, or are attached to a therapeutic candidate for targeted delivery.

FXII inhibitors may be administered to a patient before, during and/or after a medical procedure. FXII inhibitors may be administered within 1, 2, 4, 6, 12, 24, 48, 72, or 96 hours or more before, during and/or after a medical procedure. FXII inhibitors may be administered in a single dose, or in multiple doses, or repeatedly in intervals of 0.25, 0.5, 1, 2, 4, 6, 12, 24, or 48 hours or more before, during and/or after a medical procedure. FXII inhibitors may also be administered as a continuous infusion for 1, 2, 4, 6, 12, 24, 48, 72, or 96 hours or more before, during and/or after a medical procedure. Because of the advantageous property of not increasing the risk of bleeding, the FXII inhibitor may be administered before, during and/or after the medical procedure. Optimal times of administration may be determined for each particular procedure in clinical trials. The timing of administration may also depend on factors such as the type of procedure or the individual patient's condition, including the patient's history, underlying disease(s), and/or use of other medications, and may be determined by the healthcare provider.

III. FXII INHIBITORS

As discussed above, "FXII" refers to either or both of Factor XII and activated Factor XII (FXIIa). Thus "FXII inhibitor" includes inhibitors of either or both of FXII and FXIIa. Further, anti-FXII antibodies include antibodies that bind to and inhibit either or both of FXII and FXIIa. The term "FXII inhibitor" is also meant to include an inhibitor of FXII that is linked to a half-life extending polypeptide, which in one embodiment, includes a linker.

In one embodiment the FXII/FXIIa inhibitor is a specific FXII/FXIIa inhibitor, preferably a specific FXIIa inhibitor.

A specific FXII/FXIIa inhibitor refers to an inhibitor which inhibits plasmatic serine proteases other than FXII and/or FXIIa less than or equal to 25% if used in a molar ratio of 1:1. In other words: a specific FXII/FXIIa inhibitor inhibits plasmatic serine proteases other than FXII and/or FXIIa less than or equal to 25% when said inhibitor is used in a molar ratio of 1:1 of the respective plasmatic serine protease to said inhibitor. For example, a specific FXII/FXIIa mAb inhibits the plasmatic serine protease FXIa by only 5%, wherein the molar ratio of FXIa to said mAb is 1:1 whereas the same FXII/FXIIa mAb inhibits FXIIa by at least 80%, preferably at least 90%.

In one embodiment of the invention one other plasmatic serine protease is inhibited by more than 50% if used in a molar ratio of 1:1 of the respective plasmatic serine protease to said inhibitor.

In another embodiment of the invention two other plasmatic serine proteases are inhibited by more than 50% if used in a molar ratio of 1:1 of the respective plasmatic serine protease to said inhibitor.

In yet another embodiment the FXII/FXIIa inhibitor is a human FXII/FXIIa inhibitor, including a humanized monoclonal antibody, preferably a fully humanized monoclonal antibody.

A. Infestin-4

In one embodiment, the application provides a FXII inhibitor comprising Infestin domain 4, Infestin-4. In one embodiment, a FXII inhibitor comprises a variant of Infestin-4. In another embodiment, FXII inhibitors comprise Infestin domain 4, and optionally Infestin domains 1, 2, and/or 3; these proteins are known to be potent inhibitors of FXII (see WO 2008/098720; also see Campos I T N et al. 577 *FEBS Lett.* 512-516, 2004). The wild type polypeptide sequence of Infestin-4 is provided (SEQ ID NO: 1). As used herein, the term "variant" refers to a polypeptide with an amino acid mutation, wherein a "mutation" is defined as a substitution, a deletion, or an addition, to the wild type Infestin-4 sequence, wherein such changes do not alter the functional ability of the polypeptide to inhibit FXII. The term "variant" includes fragments of the wild type or mutated Infestin-4 sequence. Further examples of such variants are provided below.

In one embodiment, an Infestin-4 variant comprises the N-terminal amino acids 2-13 of the wild type Infestin-4 sequence (see underlined sequence in FIG. 2), and at least one and up to five amino acid mutations outside the N-terminal amino acids that result in differences from the wild type Infestin-4 sequence, or six conserved cysteine residues (see amino acids in bold in FIG. 2) and homology of at least 70% to the wild type Infestin-4 sequence. The N-terminal amino acids 2-13 of the Infestin-4 sequence may be important for binding to FXII based on analysis of structural data for a related inhibitor *Rhodnius prolixus* (PDB: 1 TSO) (SEQ ID NO.: 10) binding to thrombin, and analysis of SPINK-1 binding to chymotrypsin, which both share a common feature of the accumulation of contact sites in the N-terminal region as shown in FIG. 1. Therefore in one embodiment, a variant of Infestin-4 comprises the conserved N-terminal region of amino acids 2-13 of the wild type Infestin-4 sequence, and at least one and up to five amino acid mutations outside these conserved N-terminal amino acids that result in differences from the wild type Infestin-4 sequence. A mutation may be a substitution, a deletion, or an addition. As used herein, the term "outside said N-terminal amino acids" refers to any amino acid along the polypeptide chain of the variant other than the contiguous stretch of amino acids that comprises the sequence VRNPCAC-FRNYV (SEQ ID NO.: 11), i.e., amino acids 2-13 from the wild type Infestin-4 sequence. In another embodiment, an Infestin-4 variant comprises six conserved cysteine residues and has homology of at least 70% to the wild type Infestin-4 sequence. In one embodiment, the six conserved cysteine residues are amino acids at positions 6, 8, 16, 27, 31, and 48 of the wild type Infestin-4 sequence (see FIG. 2). In one embodiment, the variant comprises the final conserved cysteine. In other embodiments, the exact positions of the cysteine residues, and relative positions to each other, may change from positions 6, 8, 16, 27, 31, and 48 of the wild type Infestin-4 sequence due to insertions or deletions in the Infestin-4 variant. Nevertheless, in these embodiments, an Infestin-4 variant comprises all six cysteines and may share 70%, 75%, 85%, 90%, 91%, 92%, 93%, 94%, 95%, 96%, 97%, 98% or 99% homology to the wild type Infestin-4 sequence.

In embodiments, a variant of Infestin-4 is characterized in that it inhibits FXII. The functional activity of inhibiting FXII may be assessed for example, through in vitro and/or in vivo characterization, including direct assays to test inhibition of FXII enzyme activity, prolonged coagulation time, i.e. activated partial thromboplastin time (aPTT), or in vivo methods that evaluate coagulation. Further examples of Infestin-4 variants are SPINK-1 mutants, which are described below.

B. SPINK-1 Mutants

One embodiment involves FXII inhibitors for therapeutic use in humans. A human protein with high similarity to Infestin-4 may be employed. For example, the human protein with the highest similarity to Infestin-4 is SPINK-1, a Kazal-type serine protease inhibitor expressed in the pancreas (also known as pancreatic secretory trypsin inhibitor, PSTI). The Kazal-type serine protease inhibitor family is one of numerous families of serine protease inhibitors. Many proteins from different species have been described (Laskowski M and Kato I, 49 *Ann. Rev. Biochem.* 593-626, 1980). The amino acid sequence similarities between Infestin-4 and SPINK-1 are outlined in FIG. 2.

Based on the wild type SPINK-1 sequence (SEQ ID NO: 2) different variants may be generated in order to increase homology of the SPINK-1 sequence to Infestin-4. The phrase "increased homology to Infestin-4" refers to the process whereby amino acid mutations are made to SPINK-1 to bring the SPINK-1 sequence closer to the Infestin-4 sequence.

In one embodiment, SPINK-1 is mutated to comprise the N-terminal amino acids 2-13 of the wild type Infestin-4 sequence; the polypeptide sequence is given and is referred to as K1 (SEQ ID NO: 3). As described above, the N-terminal portion of the Infestin-4 sequence is thought to be important for FXII inhibitory function.

Therefore, in one embodiment, a variant of the mutated SPINK-1 also comprises N-terminal amino acids 2-13 of the wild type Infestin-4 sequence, and at least one and up to five amino acid mutations outside said N-terminal amino acids that result in differences from the wild type SPINK-1 sequence and which increase the homology of the variant to the wild type Infestin-4 sequence. In another embodiment, a variant of mutated SPINK-1 comprises six conserved cysteine residues and has homology of at least 70% to the wild type SPINK-1 sequence. A mutation may be a substitution, a deletion, or an addition. As defined above, the term "outside said N-terminal amino acids" refers to any amino acid along the polypeptide chain of the variant other than the contiguous stretch of amino acids that is comprised of the sequence VRNPCACFRNYV (SEQ ID NO.: 11), i.e., amino acids 2-13 from the wild type Infestin-4 sequence. The term "variant" includes fragments of said mutated SPINK-1 sequence. In one embodiment, the six conserved cysteine residues may be amino acids at positions 9, 16, 24, 35, 38, and 56 of the wild type SPINK-1 sequence (see FIG. 2). In one embodiment, the variant comprises the final conserved cysteine. In another embodiment, the exact positions of the cysteines, and relative positions to each other, may change from positions 9, 16, 24, 35, 38, and 56 of the wild type SPINK-1 sequence due to insertions or deletions in the SPINK-1 variant. Nevertheless, in these embodiments, a SPINK-1 variant comprises all six cysteines. In embodiments, a SPINK-1 variant is also characterized in that it inhibits FXII.

Examples of such SPINK-1 variants are given and are named K2, and K3 (SEQ ID NO: 4 and 5 respectively). In SPINK-1 variants K2 and K3, further amino acid substitutions outside of the N-terminus were made in order to increase homology to Infestin-4, wherein the variants are also characterized in that they inhibit FXII activity. See WO 2008/098720. FIG. 3 shows the amino acid sequence of these variants and the degree of changes to the SPINK-1 wild type sequence. In the case of the SPINK-1 variant K3, five amino acid substitutions were made to increase homology to Infestin-4. Thus in embodiments, a SPINK-1 variant may share 70%, 75%, 85%, 90%, 91%, 92%, 93%, 94%, 95%, 96%, 97%, 98% or 99% homology with the wild type SPINK-1 sequence.

C. Other FXII Inhibitors

In one embodiment, other inhibitors of FXII are administered to a patient receiving a medical procedure. As discussed above, the term inhibitors of FXII includes inhibitors of both FXII and FXIIa. In WO2006/066878 the use of antibodies against FXII or the use of inhibitors of FXII is proposed. Specifically, inhibitors to FXII include antithrombin III (AT III), angiotensin converting enzyme inhibitor, C1 inhibitor, aprotinin, alpha-1 protease inhibitor, antipain ([(S)-1-Carboxy-2-Phenylethyl]-Carbamoyl-L-Arg-L-Val-Arginal), Z-Pro-Proaldehyde-dimethyl acetate, DX88 (Dyax Inc., 300 Technology Square, Cambridge, Mass. 02139, USA; cited in: Williams A and Baird L G, 29 *Transfus Apheresis Sci.* 255-258, 2003), leupeptin, inhibitors of prolyl oligopeptidase such as Fmoc-Ala-Pyr-CN, corn-trypsin inhibitor (CTI), mutants of the bovine pancreatic trypsin inhibitor, ecotin, yellowfin sole anticoagulant protein, *Cucurbita maxima* trypsin inhibitor-V, including *Curcurbita maxima* isoinhibitors and Hamadarin (as disclosed by Isawa H et al. 277 *J. Biol. Chem.* 27651-27658, 2002), and Pro-Phe-Arg-chlormethyl-ketone (PCK).

The FXII inhibitor may be for example an antibody, or fragment of the same or mimetic retaining the inhibitory activity, for example analogues of Kunitz Protease Inhibitor domain of amyloid precursor protein as disclosed in U.S. Pat. No. 6,613,890 in columns 4 through 8. Other suitable inhibitors may be Hamadarin as disclosed in Isawa H et al. 277 *J. Biol. Chem.* 27651-27658, 2002. A suitable Corn Trypsin Inhibitor and methods of its production are disclosed in Chen Z et al. 65 *Applied and Environmental Microbiology,* 1320-1324, 1999, and in Wen L et al. 18 *Plant Mol. Biol.* 813-814, 1992.

In another embodiment, the FXII inhibitor may be an anti-FXII antibody that binds to FXII and inhibits FXII activation and/or activity. Such an antibody has been described for example in WO 2006/066878, and in Rayon et al., 1 *Blood* 4134-43, 1995. As discussed above, an "anti-FXII antibody" includes antibodies that bind to and inhibit either or both of FXII and FXIIa. Anti-FXII antibodies are described in further detail below.

D. FXII Inhibitors Linked to Half-Life Enhancing Polypeptides

Another aspect of the application provides FXII inhibitors linked to a half-life enhancing polypeptide (HLEP). In one embodiment, FXII inhibitors are small proteins. Therefore a rapid renal clearance as published for other small proteins can be expected (Werle M and Bernkop-Schnurch A, 30 *Amino Acids* 351-367, 2006). One way to address a short plasma half-life of a polypeptidic compound is to inject it repeatedly or via continuous infusion. Another approach is to increase the intrinsic plasma half-life of the polypeptide itself. For example, in one embodiment, FXII inhibitors are linked to half-life extending proteins.

A "half-life enhancing polypeptide" increases the half-life of the FXII inhibitor in vivo in a patient or in an animal. For example, albumin and immunoglobulins and their fragments or derivatives have been described as half-life enhancing polypeptides (HLEPs). Ballance et al. (WO 2001/79271) described fusion polypeptides of a multitude of different therapeutic polypeptides which, when fused to human serum albumin, are predicted to have an increased functional half-life in vivo and extended shelf-life.

The terms "albumin" and "serum albumin" encompass human albumin (HA) and variants thereof, the full mature form of which is given (SEQ ID NO: 6), as well as albumin from other species and variants thereof. As used herein, "albumin" refers to an albumin polypeptide or amino acid sequence, or an albumin variant, having one or more functional activities (e.g. biological activities) of albumin. As used herein, albumin is capable of stabilizing or prolonging the therapeutic activity of a FXII inhibitor. The albumin may be derived from any vertebrate, especially any mammal, for example human, monkey, cow, sheep, or pig. Non-mammalian albumins include, but are not limited to, albumin from hen and salmon. The albumin portion of the albumin-linked polypeptide may be from a different animal than the therapeutic polypeptide portion. See WO 2008/098720 for examples of albumin fusion proteins.

In one embodiment, an albumin variant is at least 10, 20, 40, or at least 70 amino acids long or may include 15, 20, 25, 30, 50 or more contiguous amino acids from the HA sequence (SEQ ID NO 6) or may include part or all of specific domains of HA. An albumin variant may include an amino acid substitution, deletion, or addition, either conservative or non-conservative substitution, wherein such changes do not substantially alter the active site, or active domain, which confers the therapeutic activities of the half-life enhancing polypeptides. These variants may share 70%, 75%, 85%, 90%, 91%, 92%, 93%, 94%, 95%, 96%, 97%, 98% or 99% homology.

In one embodiment, the albumin variant includes fragments and may consist of or alternatively comprise at least one whole domain of albumin or fragments of said domains, for example domains 1 (amino acids 1-194 of SEQ ID NO 6), 2 (amino acids 195-387 of SEQ ID NO 6), 3 (amino acids 388-585 of SEQ ID NO 6), 1+2 (1-387 of SEQ ID NO 6), 2+3 (195-585 of SEQ ID NO 6) or 1+3 (amino acids 1-194 of SEQ ID NO 6+ amino acids 388-585 of SEQ ID NO 6). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

In another embodiment, other proteins that are structurally or evolutionarily related to albumin may be used as HLEPs, including, but not limited to alpha-fetoprotein (WO 2005/024044; Beattie and Dugaiczyk, 20 *Gene* 415-422, 1982), afamin (Lichenstein et al. 269 *J. Biol. Chem.* 18149-18154, 1994), and vitamin D binding protein (Cooke and David, 76 *J. Clin. Invest.* 2420-2424, 1985). Their genes represent a multigene cluster with structural and functional similarities mapping to the same chromosomal region in humans, mice, and rat. The structural similarity of the albumin family members suggest their usability as HLEPs. For example, alpha-fetoprotein has been claimed to extend the half-life of an attached therapeutic polypeptide in vivo (WO 2005/024044). Such proteins, or variants thereof, that are capable of stabilizing or prolonging therapeutic activity may be used, and may be derived from any vertebrate, especially any mammal, for example human, monkey, cow, sheep, or pig, or non-mammal including but not limited to, hen or salmon. See WO 2008/098720. Such variants may be of 10 or more amino acids in length or may include about 15, 20, 25, 30, 50 or more contiguous amino acids of the respective protein sequence or may include part or all of specific domains of the respective proteins. Albumin family member fusion proteins may include naturally occurring polymorphic variants.

In another embodiment, an immunoglobulin (Ig), or variants thereof, may be used as an HELP, wherein a variant includes fragments. In one embodiment, the Fc domain or portions of the immunoglobulin constant region are used. The constant region may be that of an IgM, IgG, IgD, IgA, or IgE immunoglobulin. The therapeutic polypeptide portion is connected to the Ig via the hinge region of the antibody or a peptidic linker, which may be cleavable. Several patents and patent applications describe the fusion of therapeutic proteins to immunoglobulin constant regions to extend the therapeutic protein's half-life in vivo (US 2004/0087778, WO 2005/001025, WO 2005/063808, WO 2003/076567, WO 2005/000892, WO 2004/101740, U.S. Pat. No. 6,403,077). For example, an Fc fused to the cytokine IFN-β achieved enhanced IFN-β biological activity, prolonged circulating half-life and greater solubility (WO 2006/000448). Therefore another embodiment is to use such immunoglobulin sequences, for example, Fc fragments of immunoglobulins and variants thereof, as HLEPs. Inhibitors of FXII may be fused to Fc domains or at least portions of immunoglobulin constant regions as HLEPs and may be produced as recombinant molecules in prokaryotic or eukaryotic host cells, such as bacteria, yeast, plant, animal (including insect) or human cell lines or in transgenic animals (WO 2008/098720). A SPINK-K2-Fc fusion protein is exemplarily shown in SEQ ID NO: 7.

E. Linkers

In one embodiment, an intervening peptidic linker may be introduced between the therapeutic polypeptide and the HLEP. In one embodiment, a cleavable linker is introduced, particularly if the HLEP interferes with the therapeutic polypeptide's specific activity, e.g. by steric hindrance. In certain embodiments, the linker is cleaved by enzymes such as coagulation proteases of the intrinsic, extrinsic, or common coagulation pathway. Coagulation proteases of the intrinsic pathway are proteases in the contact activation pathway, including, for example, FXIIa, FXIa, or FIXa. In one embodiment, the linker is cleaved by FXIIa. Proteases of the extrinsic pathway include proteases in the tissue factor pathway, for example, FVIIa. Proteases of the common pathway includes proteases involved in the conversion of fibrinogen to fibrin, for example, FXa, FIIa, and FXIIIa.

F. Therapeutic Formulation and Administration

The FXII inhibitor or variant thereof may have a purity greater than 80%, or greater than 95%, 96%, 97%, 98%, or 99% purity. In one embodiment, the variant may have a pharmaceutically pure state that is greater than 99.9% pure with respect to contaminating macromolecules, such as other proteins and nucleic acids, and free of infectious and pyrogenic agents.

The purified FXII inhibitor may be dissolved in conventional physiologically compatible aqueous buffer solutions to which there may be added, optionally, pharmaceutical excipients to provide pharmaceutical preparations for treating SBI in a patient. Such pharmaceutical carriers and excipients as well as suitable pharmaceutical formulations are well known in the art. See for example Kibbe et al. Handbook of Pharmaceutical Excipients, (3rd ed., *Pharmaceutical Press*), 2000. The pharmaceutical composition may be formulated in lyophilized or stable soluble form. The polypeptide may be lyophilized by a variety of procedures known in the art. Lyophilized formulations are reconstituted prior to use by the addition of one or more pharmaceutically acceptable diluents such as sterile water for injection or sterile physiological saline solution.

Formulations of the FXII inhibitor are delivered to the patient by any pharmaceutically suitable means of administration. Various delivery systems are known and can be used to administer the composition by any convenient route. The compositions may be administered systemically, such as parenterally. The term "parenteral" as used here includes subcutaneous, intravenous, intramuscular, intra-arterial and intra-tracheal injection, instillation, spray application and infusion techniques. Parenteral formulations may be administered intravenously, either in bolus form or as a constant infusion, or subcutaneously, according to known procedures. Preferred liquid carriers, which are well known for parenteral use, include sterile water, saline, aqueous dextrose, sugar solutions, ethanol, glycols, and oils. For systemic use, the therapeutic proteins may be formulated for an intravenous line or an arterial line. The formulations may be administered continuously by infusion or by bolus injection. Some formulations encompass slow release systems. In one embodiment, the formulation is administered as a patch. Tablets and capsules for oral administration may contain conventional excipients such as binding agents, fillers, lubricants or wetting agents, etc. Oral liquid preparations may be in the form of aqueous or oily suspensions, solutions, emulsions, syrups, elixirs or the like, or may be presented as a dry product for reconstitution with water or other suitable vehicle for use. Such liquid preparations may contain conventional additives, such as suspending agents, emulsifying agents, non-aqueous vehicles, and preservatives.

The dose of the FXII inhibitor may depend on many factors such as, e.g. the indication, formulation, or mode of administration and may be determined in preclinical and clinical trials for each respective indication. The dose of FXII inhibitor may be administered to a patient before, during and/or after a medical procedure. In one embodiment, the FXII inhibitor may be administered within 1, 2, 4, 6, 12, 24, 48, 72, or 96 hours before, during and/or after a medical procedure. A FXII inhibitor may be administered in a single dose, or in multiple doses, as a continuous infusion for a period of time for 0.25, 0.5, 1, 2, 4, 6, 12, 24, or 48 hours, or repeatedly in intervals of 0.25, 0.5, 1, 2, 4, 6, 12, 24, or 48 hours before, during and/or after a medical procedure. Because of the advantageous property of not increasing the risk of bleeding, in one embodiment, the FXII inhibitor is administered during the procedure. The pharmaceutical composition may be administered alone or in conjunction with other therapeutic agents. These agents may be co-formulated, or may be administered as separate formulations either concurrently or separately and via the same route of administration or different routes of administration. The schedule of administration or dose of a FXII inhibitor may also vary between individual patients with the same indication or different indications depending on factors such as other medical conditions or therapies.

IV. ANIMAL MODEL OF SBI

One aspect of the application pertains to an animal model of ischemia that mimics the heterogeneous mechanisms and sources of an embolus that can lead to ischemic injury in at least one target organ. In one embodiment, the animal model comprises a procedure, wherein the procedure comprises release of at least one embolus in the arterial system of an animal that could result in an ischemic injury in at least one target organ, wherein the target organ is brain, heart, kidney, liver, and/or gastrointestinal tract organ (including the esophagus, stomach, small intestine, and/or large intestine (including colon and/or rectum) and further wherein, if the target organ is the brain, wherein the ischemic injury is characterized as clinically silent and/or the embolus is nonthrombolysable. In one embodiment, the target organ is the brain. In one embodiment, the animal is evaluated for an indication of an ischemic injury in the brain that is clinically silent. In certain embodiments, the animal also receives a therapeutic candidate to test for the therapeutic candidate's ability to reduce an ischemic injury in the target organ. The term "clinically silent" is defined above. In this embodiment, mice are clinically assessed to evaluate if an ischemic injury in the brain is "clinically silent", i.e. the animal is assessed for acute, overt behavioral or motor deficits associated with stroke. Indicators of stroke, include, but are not limited to, dyskinesia, lethargy, grip, limb weakness, eyelid droop, gait disturbance, circling, and rolling. An animal that does not exhibit stroke-like symptoms following administration of an embolus may have an ischemic injury in the brain that is clinically silent.

The animal model also involves the evaluation of the animal for indication of an ischemic injury in the brain. In one embodiment, the evaluation involves imaging. An "indication" of ischemic injury may be evident to one of skill in the art by evaluating images of the brain. For example, an ischemic injury that results in tissue damage may be evident by physical changes in the appearance of the tissue on brain images, or by evidence of inflammation, clotting, or edema in or around an area of the brain. For example, diffusion-weighted MRI (DWI) may be used to visualize ischemic injury, as the diffusion of molecules differs in and around injured tissue.

The animal model is considered to be a nontherapeutic model, namely it is a research tool for evaluating the clinical impact of an embolus. In this model, an embolus is intentionally released in the animal with the intent of causing ischemia, and such an embolus would create an ischemic injury if no other steps were taken. In other words, the animal's health and well-being is not improved by the procedure and therefore it cannot be considered to be a therapeutic, nor can it be considered to be a beneficial surgical procedure. The animal is sacrificed during the evaluation process or at the conclusion of the evaluation. Nevertheless, in one embodiment, the animal model may be useful for evaluating a therapeutic candidate to treat ischemia. In these embodiments, although a therapeutic candidate may have a therapeutic result in the animal model, it is the therapeutic candidate and not the animal model, that is considered to be therapeutic.

A. Animals

The animal model is further characterized in that the animal may be a mammal including, but not limited to, a mouse, rat, rabbit, cat, dog, pig, or monkey. For example, the animal may be a mouse or a rat. The animal may be male or female and of any age. Examples of murine strains that may be used include, but are not limited to, BALB/c, C57/BL6, C57/CL10J, CBA/J, DBA/J, FVB/J, C3H/HeJ, A/J, AKR/J, 129S1/SvImJ, 129X1/SvJ, NOD, SJL, TALLYJO/JngJ, MRL, NZW, sub-strains and hybrid strains. Examples of rat strains that may be used include, but are not limited to, CD, Wistar, Fisher, Sprague Dawley, BBDP, Long-Evans, Zucker, Hairless rats, and sub-strains, and hybrid strains.

In one embodiment, the animal of the animal model is modified, such as a genetically modified animal or an animal that has been altered in another way, such as by a procedure or administration of a substance. A genetically modified animal may have a gene(s) knocked out or knocked in, or a gene(s) that is conditionally knocked out or knocked in. The animal may be characterized in that it is used as a model for another disease. For example, an animal may susceptible to another disease due to the genetic background, or due to receiving an agent or procedure that induces a disease or altered condition (e.g. an autoimmune disease, such as in NOD mice, or in MOG-induced EAE). It may be of interest to use the animal model to study SBI in such modified states or disease contexts.

B. Embolus

In one embodiment, a nonthrombolysable embolus is administered to an animal to mimic at least one embolus that may be introduced during a medical procedure. As used herein, the term "nonthrombolysable" refers to an embolus that is not lysed with thrombolytic drugs (i.e. the embolus is not composed of blood). In these embodiments, the procedure releases an embolus that is not a thrombus. Examples of a nonthrombolysable embolus include, but are not limited to, bubbles, oil, fat, cholesterol and/or debris, as these emboli are not lysable with thrombolytic drugs.

In one embodiment, an embolus is a solution of microbubbles that mimics contrast agents used in imaging techniques such as ultrasound. Capillaries and arterioles in the brain may thus be occluded in a diffuse rather than focal distribution.

In one embodiment, a microbead is used to mimic a non-lysable embolus and is characterized in that administration does not result in overt stroke-like symptoms. The term "microbead" includes microspheres and other microparticles (such as a microparticle that is not uniformly spherical in shape). In one embodiment, a microbead is used to mimic a nonthrombolysable embolus. The size of the microbead may be for example, any size from 20-200 µm, 25-100 µm, or 30-50 µm. The amount of microbeads administered may be 500, or 1000, or 2000 microbeads, including any amount from 500-600, 500-700, 500-800, 500-900, 500-1000, and 500-2000 microbeads. The number of microbeads may vary depending on the size of the animal, the type and size of microbead, and other experimental factors. A microbead may be made of natural or synthetic materials, including, but not limited to, polystyrene, polyethylene or other polymers, latex, glass, ceramic, metal, quantum dot, or paramagnetic material. In one embodiment, the microbead is fluorescent, which may allow for tracking of embolic materials. Fluorescent dyes include, but are not limited to, coumarin, fluorescein, rhodamine, or phycoerythrin, or conjugates thereof. Microbeads may be internally dyed or conjugated to a fluorescent dye. One advantage to using microbeads for administration is they are easily standardized, wherein the size and amount of microbeads may be quantified and the amount administered may be kept constant across multiple animals.

In another embodiment, an embolus is administered to an animal, wherein the embolus comprises coagulated blood. The coagulated blood may be reduced into small fragments, using techniques such as tissue homogenization or sonication. The source of the coagulated blood may be from the blood of the same animal that receives the administration, or from an animal of the same strain or species, or from an animal of a different strain or species than the animal receiving the administration. Coagulation may be induced using known coagulation reagents, such as $CaCl_2$, thrombin, or human thrombin. In one embodiment, coagulated blood is made fluorescent, for example, by using a contrast agent or blood pool agent, such as a near-infrared blood pool agent.

In another embodiment, an embolus is released in the arterial system of an animal using a catheter. In another embodiment, an embolus is released in the arterial system of an animal due to a procedure that comprises clamping and/or surgery.

C. Procedure

In one embodiment, at least one embolus is injected into the arterial system of an animal. The embolus may be injected into any artery, including the aorta, the aortic arch, a carotid artery, a coronary artery, the brachiocephalic artery, the vertebrobasilar circulation, intracranial arteries, renal artery, a hepatic artery, a mesenteric artery, and/or a blood vessel of the arterial system cranial to the heart.

In one embodiment, the embolus is injected into a carotid artery. In one embodiment, an artery is clamped. In certain embodiments, a temporary ligation is tied around an artery, such as around a carotid artery. In one embodiment, the embolus may be administered via intracardiac injection, but this approach has several disadvantages. In this embodiment, the embolus is distributed throughout the entire animal, making standardization more difficult because it is unclear how many emboli lodge in the brain. In addition, the mortality of the procedure is high, and it may not be clear if the injection was successful. In certain circumstances, intracardiac injection may be useful for evaluation of ischemia to target organs, e.g., heart, kidney, liver, and/or gastrointestinal tract organ, including the esophagus, stomach, small intestine, and/or large intestine (including colon and/or rectum).

In one embodiment, a tube or a catheter is used to administer the embolus. The catheter may be an arterial catheter. A catheter may be made of polyethylene, polyurethane, or other polymers or materials. The catheter may be of an appropriate size for the site of injection and for the size of the animal. A catheter may be modified to aid in the injection of the embolus, for example, a catheter can be modified by stretching the tubing to manually achieve a narrower, thinner, or pointier catheter suitable for use in a small laboratory animal. In one embodiment, an injection needle is used, wherein one of skill in the art can technically inject an embolus into the arterial system of an animal.

D. Evaluation

In embodiments, the animal model comprises an evaluation step. The evaluation may comprises in vivo or ex vivo techniques, such as imaging and/or histology. Imaging techniques include, but are not limited to, radiology or nuclear medicine, e.g. CT including SPECT-CT and/or FMT-CT; MRI including diffusion-weighted MRI (DWI) or fMRI; PET; optical imaging, such as fluorescence reflectance imaging; ultrasound, microscopy, fluoroscopy, autoradiography, and/or phosphor imaging. Histology and/or staining techniques may be performed, such as TTC staining, immunohistochemistry and/or histochemistry.

In one embodiment, the animal model can be used with molecular imaging techniques to evaluate physiological processes, such as inflammation, blood clotting, or complement activation that may occur due to release of an embolus. For example, a molecule involved in a physiological process of interest may be labeled with a contrast agent, radioisotope or dye that is appropriate for the imaging modality. Dyes and contrasts that are used in various imaging modalities are described above and are well known to one of skill in the art. See for example, Pysz M A et al. 65 *Clinical Radiology* 500-516, 2010.

E. Therapeutic Candidates

In another embodiment, the animal model may be useful for the evaluation of a therapeutic candidate to treat SBI. The term "ability to reduce" as used in the phrase "the therapeutic candidate is tested for its ability to reduce an ischemic injury in the brain", is meant to be understood as any therapeutic candidate that is tested where the purpose of testing the therapeutic candidate is to evaluate if it can reduce an ischemic injury, i.e. if the therapeutic candidate can limit or treat an SBI. Therefore, a test therapeutic candidate may be administered in an animal model of SBI, and its ability to reduce an ischemic injury in the brain is evaluated. The evaluation may reveal that the therapeutic candidate decreases, increases, or results in no change in the amount of ischemic injury or conditions associated with ischemic injury in the brain.

In one embodiment, the therapeutic candidate is administered to the animal before, during and/or after the procedure. The evaluation may be performed once, or multiple times throughout the testing. For example, in vivo imaging may be performed before, during, and/or after the procedure or administration of the therapeutic candidate. Controls may include an animal that does not receive the therapeutic candidate or may include imaging an aminal before and after the procedure or administration of the therapeutic candidate.

In one embodiment of the animal model, the therapeutic candidate may be administered within 1, 2, 4, 6, 12, 24, 48, 72, or 96 hours or more before, during and/or after the procedure. The therapeutic candidate may be administered in a single dose, or in multiple doses, or repeatedly in intervals of 0.25, 0.5, 1, 2, 4, 6, 12, 24 or 48 hours or more before, during and/or after the procedure. In one embodiment, the therapeutic candidate is a FXII inhibitor. Because of the advantageous property of not increasing the risk of bleeding, the FXII inhibitor may be administered during the procedure and/or before and/or after the procedure. The dose of the therapeutic candidate may depend on the properties of the therapeutic candidate, such as half-life or toxicity, or may depend on the type or size of animal used, or the condition of the animal being used, and may need to be determined empirically. For example, in one embodiment, the dose of FXII inhibitor is 1 mg/kg, 50 mg/kg, 100 mg/kg, 200 mg/kg, 500 mg/kg, 1000 mg/kg, or from 1-1000 mg/kg, or 50-500 mg/kg, or 100-200 mg/kg. The dose of the therapeutic candidate may be administered to the animal via any method used to administer a therapeutic candidate to an animal. In one embodiment, the therapeutic candidate is administered systemically. In one embodiment, the therapeutic candidate is administered via intravenous tail vein injection.

In one embodiment, the therapeutic candidate is an antibody. An antibody may be in the form of a full length Ig, Fab, F(ab)$_2$, Fv, scFv, or other form or variant thereof. The antibody may be monoclonal or polyclonal. The antibody may be characterized in that the isotype is IgM, IgD, IgA, IgG, or IgE, or variants thereof. The antibody may be from a mammalian species, including, but not limited to human, mouse, rat, rabbit, goat, hamster, or monkey. The antibody may be humanized or CDR-grafted. The antibody maybe mutated or modified to alter immunogenicity, half-life, or to impart other advantageous properties associated with a therapeutic antibody. In one embodiment, the antibody inhibits a molecule involved in the pathophysiology of SBI. In one embodiment, the antibody is an anti-FXII antibody. In this embodiment, the antibody may bind to an epitope on the heavy chain or light chain of FXII (wherein, "FXII" includes FXII and FXIIa), such as a neutralizing epitope. The antibody may be high affinity and/or high avidity for binding to FXII. The antibody may have the property of being able to recognize more than one antigen. The antibody may be conjugated to a polypeptide, nucleic acid or small molecule.

In another embodiment, the therapeutic is a protein, peptide, nucleic acid, or small molecule. The term "small molecule" refers to a low molecular weight compound. A small molecule may be for example less than 1000 daltons, allowing diffusion across cell membranes. A small molecule may be characterized in that it binds with high affinity to a molecule of the coagulation pathway, or FXII, or a molecule involved in the pathophysiology of SBI. A preferred small molecule is one which can be resorbed from the GI tract.

The embodiments are further illustrated by the following examples which should not be construed as limiting. Other embodiments will be apparent to those skilled in the art from consideration of the specification and practice of the embodiments disclosed. The contents of all references, patents and published patent applications cited throughout this application are hereby incorporated by reference.

EXAMPLES

Example 1

Production of Infestin-4 and rHA-Infestin-4

The Infestin-4 complementary DNA sequence was synthesized and extended with a coding sequence for a linker (Gly-Gly-Ser)$_3$ (SEQ ID NO.: 12) in its 5 position and inserted into BamH1 and NotI sites of pIRESpuro3 (BD Biosciences, Heidelberg, Germany). Albumin complementary DNA was amplified by PCR with the forward primer 5-GCGGCTAGCATGAAGTGGGTAACCTTT-ATTTCCC-3 (SEQ ID NO: 8) and the reverse primer 5-GCGGGATCCTCCTAAGCCTAAGGCAGCTT-GACTTG-3 (SEQ ID NO: 9). The amplicon was digested with NheI and BamH1 and inserted into the NheI/BamH1 sites of the Infestin-4 vector. The resulting vector, capable of expressing a fusion protein consisting of albumin-linker Infestin-4 (rHA-Infestin-4), was grown in *Escherichia coli* TOP10 (Invitrogen, Karlsruhe, Germany) and purified using standard protocols (Qiagen, Hilden, Germany). HEK-293 cells were transfected with Lipofectamine 2000 reagent (Invitrogen) and grown in serum-free medium (Invitrogen 293 Express) in the presence of 4 µg/mL puromycin. Transfected cell populations were grown in fermenters, Supernatant was harvested for purification of the produced fusion protein. rHA-Infestin-4 was purified by immune affinity chromatography. Fermentation supernatant was applied to an equilibrated anti-albumin column. The product was eluted with a glycine buffer (pH 2.5). See WO 2008/098720; Hagedorn I et al. 117 *Circulation* 1153-1160, 2010.

A (His)$_6$-tagged Infestin-4 construct was generated and was found to have a shorter half-life when compared to the rHA-Infestin-4 construct. See WO 2008/098720; Hagedorn I et al. 117 *Circulation* 1153-1160, 2010. The (His)$_6$-tagged Infestin-4 was purified by copper metal chelate chromatography on POROS MC 20. Fermentation supernatant was applied on a copper sulfate-loaded column, equilibrated with phosphate-sodium chloride buffer (pH 7.7). (His)$_6$-tagged Infestin-4 was subsequently eluted in an imidazole gradient.

Example 2

Animal Models of SBI

The application provides realistic animal models that reflect the heterogenous mechanisms leading to SBI. In one embodiment of the animal model, ischemic injury may be induced by microbeads which emulate nonthrombolysable emboli such as air or fat that can result from e.g. vascular procedures and surgeries. In another embodiment of the animal model, ischemic injury may be induced by coagulated blood that may result from disturbances in the coagulation cascade or vascular wall injury.

All experiments were performed in adult Balb/c mice (25-30 g; n=24), obtained from Charles River Laboratories, Inc. (Wilmington, Mass.). The Institutional Review Board approved all animal experiments. Animals were physiologically monitored during and after all procedures. Mice were anesthetized in an isoflurane chamber with 2% isoflurane by inhalation with 2 L/min of supplemental oxygen and transferred to a warm heating pad in a supine position while under isoflurane. Using procedures described below, microbeads or ex vivo formed coagulated blood were injected one-sided retrogradely through the external carotid artery into the internal carotid artery while the common carotid artery was temporarily occluded to force the embolus into the arterial system of the brain without compromising perfusion.

A. Procedure

After the animal was anesthetized, the neck was shaved and Nair was applied for complete hair removal. The neck was then swabbed with isopropyl alcohol and draped with sterile gauze. A vertical incision was made to the neck, and the exposed parotid gland was moved aside. The common, internal, and external carotid arteries were identified and isolated. 10-0 Ethicon nylon sutures (Johnson & Johnson, Brussels, Belgium) were used for all arterial ligations. Two 10-0 sutures were tied around the external, one around the internal, and one around the common carotid artery. The two sutures around the external carotid artery were then tied, and then the artery was cut between them. At this point, mice in a control group, who received ligation of the external carotid artery alone, underwent no further intervention in order to ensure that this part of the procedure would not result in any brain injury. Temporary ligations were then tied around the common and internal carotid arteries. A modified Intramedic polyethylene PE10 catheter (I.D. 0.28 mm, I.D. 0.61 mm, Becton Dickinson and Company, Sparks, Md.) was inserted into the proximal open end of the external carotid artery and sutured in place. The catheter was a standard PE10 catheter that was modified by gently applying traction and stretching the tubing manually to achieve a slightly narrower lumen and diameter. The ligation on the internal carotid artery was then released allowing for flow only to the internal carotid artery into the arterial system feeding the brain. Flashback of arterial blood into the catheter was observed, and then either prepared microbeads or coagulated blood was injected (FIG. 4).

For the fluorescent microbeads, it was determined that an intracarotid injection of approximately 500 microbeads resulted in reproducible, clinically silent micro-lesions. A syringe loaded with approximately 500 Fluoresbrite™ Plain YG 45 Microspheres (Polysciences, Inc., Warrington, Pa., 42.58±0.8 μm diameter, Excitation max.=441 nm, Emission max.=486 nm) was attached to the catheter and injected (FIG. 4A+D).

For the fluorescent coagulated blood, 500 μL of fresh heterologous mouse blood was withdrawn from donor mice via cardiac puncture and immediately added to sodium citrate solution for initial anticoagulation (final concentration, 0.32%). 20 μmol $CaCl_2$ was added to the plasma, followed by 10 units of high activity human thrombin to induce coagulation (Calbiochem®, EMD Chemicals, Inc., Darmstadt, Germany, MW 37,000, 100 units/mL, specific activity 2800 NIH units/mg protein). After blood was allowed to coagulate at room temperature for one hour, 2 nmol of Genhance 680TM, a near-infrared blood pool agent (VisEn Medical, Bedford, Mass.) was added for incubation at 4° C. for 72 hours. This allowed for fluorescent staining of the coagulated blood for later ex vivo detection via fluorescence imaging. This time period allowed for contraction and stabilization of the coagulated blood. When ready for use, the coagulated blood was removed and washed with normal saline. 250 μL of normal saline was added to the coagulated blood and then a tissue homogenizer was used to reduce the coagulated blood into small particles (FIG. 4B). 10 μL of this fluorescent microemboli solution was then drawn into a syringe and injected.

After injection of either microbeads or coagulated blood, the catheter was removed and the suture that had been holding the catheter in place was pulled to close the external carotid artery. The ligatures at the internal carotid and common carotid arteries were then reopened to restore blood flow to the brain, and the parotid gland was replaced and the skin sutured with 7-0 nylon suture. The animal was returned to its cage and allowed to recover.

After recovery from anesthesia, the mice were assessed for overt behavioral and motor deficits. Each animal was observed for dyskinesia, lethargy, grip, limb weakness, eyelid droop, gait disturbance, circling, and rolling. Observation of any of the above symptoms was considered to be an indicator of stroke, while lack of the above symptoms indicated that no overt stroke had occurred, consistent with the possibility of SBI. If no stroke symptoms were present, the mice were used for further evaluation of SBI. Otherwise the mice were excluded from further evaluation of SBI and sacrificed.

B. Treatment Groups

After optimization of SBI models, 4 cohorts were studied (n=5-7 per group): Mice with induction of SBI by coagulated blood or microbeads (untreated controls), and 2 additional groups in which mice were treated with rHA-Infestin-4 at a dose of 200 mg/kg via intravenous tail vein injection. The mice received their first injection immediately after SBI induction. Single Photon Emission Computed Tomography—Computed Tomography (SPECT-CT) imaging of FXIII activity was done 3 hours after SBI. The cohorts that were imaged three days after SBI by MRI received daily injections until and including on day 3 after injury. Triphenyltetrazolium chloride (TTC) staining was assessed 3 days after SBI.

C. MRI

Inflammation was assessed by MRI (myeloperoxidase (MPO)-Gd, day 3). MRI was performed using a Bruker 4.7T scanner with a RARE T1 scan (TR: 1500 ms, TE: 8.48 ms, Avg: 8, Matrix: 192×192×22, Voxel Size: 0.133 mm×0.13 mm×0.5 mm), a RARE T2 with the same geometry (TR: 5622.893, TE: 20 ms, Avg:4) and a diffusion weighted image (DWI) using an EPI diffusion weighted sequence with 6 diffusion directions (TR: 4800 ms, TE: 32 ms, Matrix: 128×128×22, Voxel Size: 0.195 mm×0.195 mm×0.5 mm).

Mice were scanned before and every 15 min up to 90 min after intravenous administration of 0.3 mmol/kg of myeloperoxidase-gadolinium contrast agent diluted in 10% DMSO. The mice were then sacrificed, perfused and brains were harvested and sliced for fluorescence imaging on the OV-100 microscope (Olympus) to verify that SBI occurred.

For data analysis, Amira software (Visage Imaging, San Diego, Calif.) was used. Regions of interest (ROIs) were identified on each image slice of the 90 minute post injection T1 scans. The brain ventricles were excluded individually prior to automated segmentation of MPO positive areas, and this segmentation was verified by a board certified radiologist. The MPO positive voxels were automatically identified by signal intensity of 1.25 times the average normal brain background signal. The signal amplitude values were divided by the standard deviation of the noise from a ROI outside the body of the mouse to calculate the contrast to noise ratio (CNR) of MPO positive voxels. T2 images were segmented in a similar manner for 3D visualization.

D. SPECT-CT

Coagulation was assessed by SPECT-CT (FXIII-Ind, 3 hours). The groups of mice underwent SBI induction and treatment one hour prior to injection of approximately 1 mCi of a FXIII-substrate peptide labeled with indium-111 (actual amount injected was 731-1273 µCi). Two hours post injection, SPECT-CT was performed using the Gamma Medica-Ideas X-SPECT small animal imaging system. The CT scan was performed using a cone beam (50 kVp, 500 mA) x-ray tube with a solid state CMOS detector over 256 projections. These projections were reconstructed using the modified feldkamp reconstruction algorithm. The SPECT scan utilized dual gamma cameras with 1 mm medium energy pinhole collimators through 64 projections (32 projections from each camera) at 90 s/projection. The SPECT images were reconstructed using the ordered subsets expectation maximization algorithm (OSEM) and fused to the CT images for accurate anatomical colocalisation of molecular information.

Animals were sacrificed immediately after SPECT-CT imaging with a blood sample taken. The animal was perfused with 20 ml of saline. A muscle sample was taken; the brain was excised and, along with the blood sample, counted on a Wallac Wizard 1480 gamma well counter. The brain was then sliced into 2 mm sections and imaged on the Olympus Biosystems OV-100 fluorescent scanner. The brain slices were imaged on both sides. Afterward the slices were placed on phosphorimager plates overnight for autoradiography. The plates were read on a Molecular Dynamics Typhoon phosphorimager plate reader.

For SPECT-CT data analysis, the brain and muscle were manually segmented from the CT images using Amira software to calculate the target to background ratio (TBR) of the brain to muscle. Data were normalized for the mass of the brain and the injected dose of each animal. Autoradiography, gamma counting and SPECT data were decay corrected. 3D visualizations of the SPECT-CT data were reconstructed using Osirix software (Pixmeo, Geneva, Switzerland).

E. Ex Vivo Assessment

After MRI and SPECT-CT imaging studies were completed, the animals were sacrificed and the brains removed.

If the mouse was part of the SPECT-CT subgroup, the brain was first measured for overall radiation activity by scintillation counting. The fresh brain was then cut into 2 mm thick coronal sections using a mouse brain slicer (Zivic Instruments, Pittsburgh, Pa.). All brains were then immediately imaged with an OV-100TH Small Animal Imaging System (Olympus, Center Valley, Pa.), a hybrid of a planar reflectance fluorescence imaging system and a high-power microscope. The brain sections were imaged using bright field and the GFP fluorescence channel (excitation 400 nm, emission 508 nm) for the microbeads and the near-infrared channel for the fluorescent coagulated blood (emission 680 nm) with up to 16-times magnification. Depending on the chosen resolution, wavelength, and magnification, image acquisition times ranged between 5 ms and 60 seconds per frame for the images. White light images were also acquired with a digital camera to assess potential hemorrhage caused by injury. For mice in the SPECT-CT study, the brain slices were then placed on a phosphor imager overnight.

If the mouse was part of the MRI subgroup, the brain slices were placed into a 1% TTC in PBS solution for 30 minutes at 37° C. The brain sections were then washed three times with PBS for one minute each. The brain was then imaged using a digital camera (Olympus FE-280) to assess TTC staining. Viable brain tissue stained red with TTC, while infarcted regions did not stain. For mice used for immunohistochemistry (IHC), a central brain slice was stained with TTC, while adjacent slices were embedded for IHC.

For further histological analysis, the adjacent slices of brain tissue were embedded in O.C.T. compound (Sakura Finetek, Torrance, Calif.), and serial 5 µm frozen sections were cut. The avidin-biotin peroxidase method was used for IHC and tissue sections were incubated with FXIII antibody: C-20 (Santa Cruz Biotechnology, Inc., Santa Cruz, Calif.) followed by biotinylated anti-goat IgG secondary antibody (Vector Laboratories, Inc., Burlingame, Calif.). The reaction was visualized with a 3-amino-9-ethylcarbazole (AEC) substrate (DakoCytomation, Carpinteria, Calif.) and all sections were counterstained with Harris hematoxylin solution. The slides were digitized automatically at magnification 400 and images were captured using Nanozoomer HT1.0 (Hamamatsu, Japan).

Results are expressed as mean±SEM. Statistical comparisons between two groups were evaluated by Student's t-test and corrected by ANOVA for multiple comparisons. A value of $p<0.05$ was considered to indicate statistical significance. The same statistical analyses were used throughout the examples when p values are noted.

Figure 5:
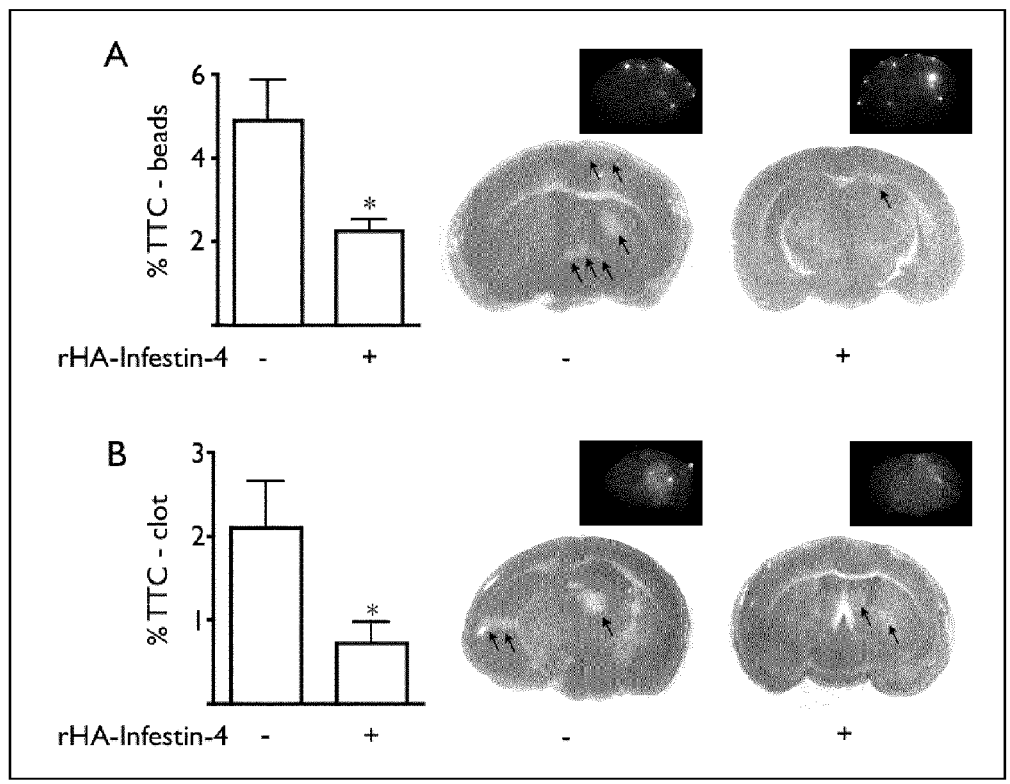
FIG. 5. rHA-Infestin-4 reduces injury quantified by triphenyltetrazolium chloride (TTC). Assessment of tissue damage by TTC staining on day 3 after administration of an embolus is shown in bar graphs. Representative TTC slices and fluorescence reflectance images of the corresponding brain section are shown. Data are presented as mean±standard error of mean. * p<0.05.

Both models produced cerebral vascular occlusions in small vessels (FIG. 4D+E) that can result in clinically silent cerebral ischemia (FIG. 5).

Both models produced small infarcts (FIG. 5) that occupied <5% of the overall brain, as assessed by TTC staining. The microbeads method produced slightly more tissue damage compared to the coagulated blood model. Lesions were observed primarily on the side of injection.

Example 3

Treatment of SBI with rHA-Infestin-4

After treatment with rHA-Infestin-4, mice in both SBI models experienced significantly fewer microinfarcts with >50% reduction in the infarcts detected by the TTC stain. There was slightly more reduction in the infarct area in the coagulated blood model (66% reduction, FIG. 5B) compared to that of the microbead model (54% reduction, FIG. 5A). The microbead model mimics emboli from substances that do not directly affect the coagulation pathway; however rHA-Infestin-4 also reduced the infarcted areas in this model.

Figure 6:
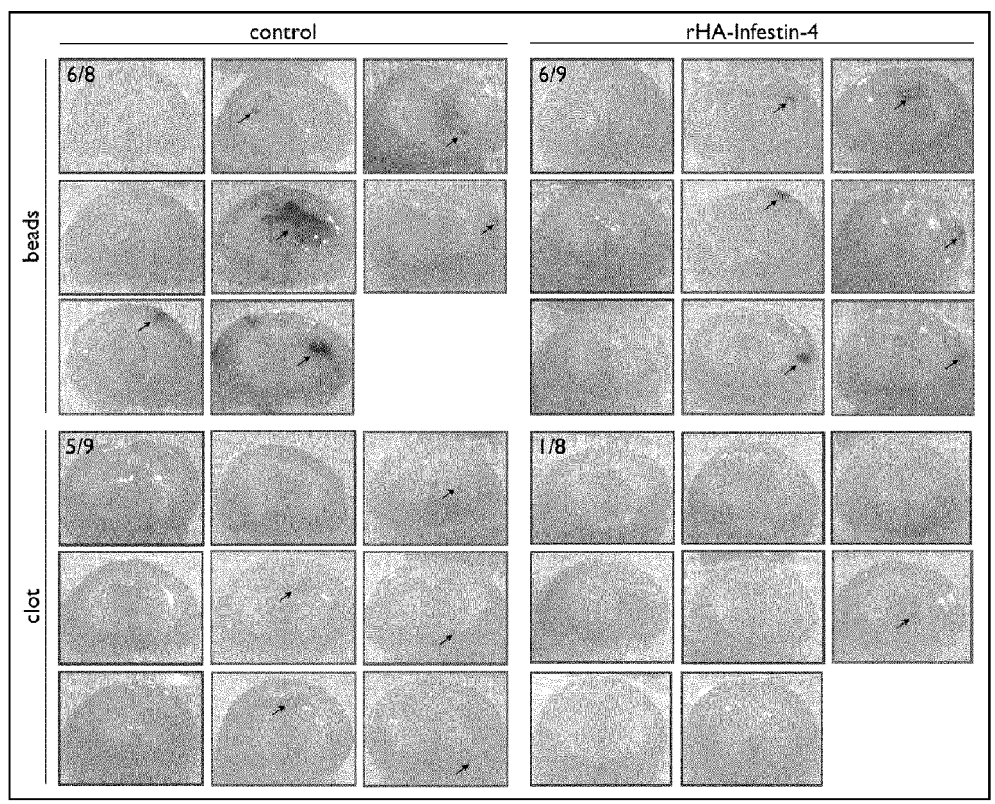
FIG. 6. Secondary hemorrhage is not increased by rHA-Infestin-4 (day 3). Assessment of secondary hemorrhage on day 3 after injection of beads or coagulated blood. One representative brain slice is shown per mouse. Red frames indicate mice in which hemorrhage was detected (arrows).

Relatively frequent evidence of microhemorrhages were found in both SBI models, with 6/8 (75%) of mice in the microbeads model and 5/9 (56%) of the mice in the thromboemobli model (FIG. 6). However, after rHA-Infestin-4 administration an increased frequency of microhemorrhage was not found in either model. In fact, there was possibly a decreased microhemorrhage rate in the coagulated blood model (only ⅛ animals had microhemorrhage, FIG. 6, bottom right).

Interestingly, similar to previous studies on stroke (Kleinschnitz C et al., *J Exp Med.,* 203:513-518, 2006; Hagedorn I et al. *Circulation,* 121:1510-1517, 2010), an increased frequency of hemorrhage in SBI was also not found, with a lower rate of hemorrhage in the coagulated blood model after rHA-Infestin-4 treatment. While this lower rate will need to be corroborated and further studied, it implies that rHA-Infestin-4 may decrease vascular injury caused by coagulated blood. In addition, it has clinical relevance because it points to a favorable profile of unwanted side effects since general anticoagulatory therapy usually carries an increased risk of bleeding. This was not the case in our current study.

Example 4 rHA-Infestin-4 Decreases FXIII Activity in SBI

Figure 7:
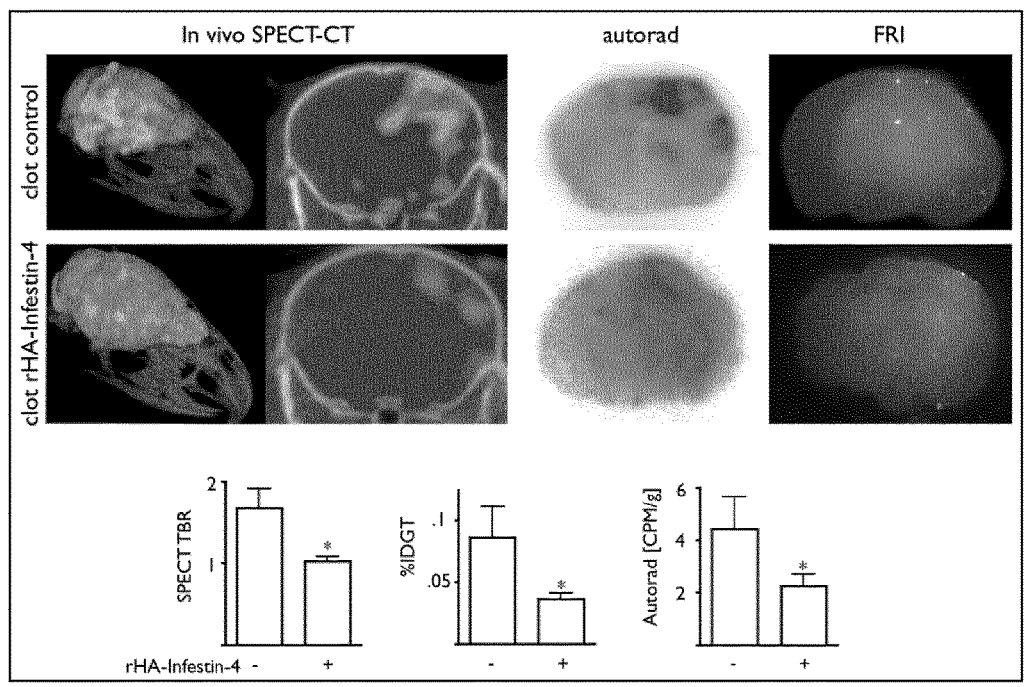
FIG. 7. rHA-Infestin-4 reduces FXIII activity in injured area after administration of coagulated blood assessed by SPECT-CT. Plasma transglutaminase activity (FXIIIa) was assessed 3 hours after administration of an embolus comprised of coagulated blood. FRI: Fluorescence reflectance imaging showing location of coagulated blood. % IDGT refers to injected dose per gram tissue. TBR: Target to background ratio. Data presented as mean±standard error of mean. * p<0.05.
Figure 8:
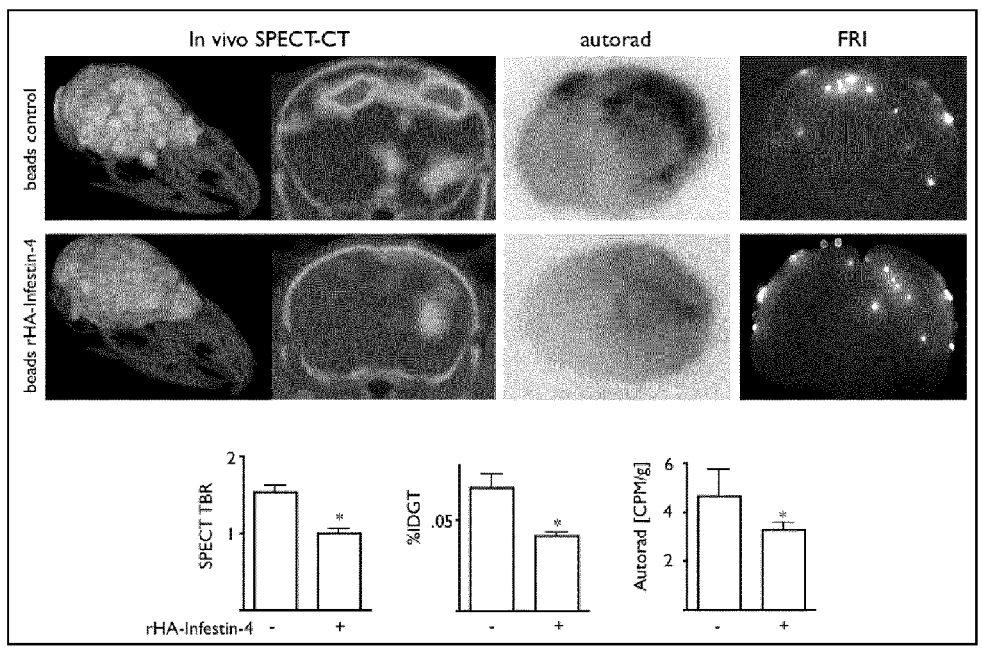
FIG. 8. rHA-Infestin-4 reduces FXIII activity in injured area after administration of microbeads assessed by SPECT-CT. Plasma transglutaminase activity (FXIIIa) was assessed 3 hours after application of bead emboli. FRI: Fluorescence reflectance imaging, showing location of beads. % IDGT refers to injected dose per gram tissue. TBR: Target to background ratio. Data are presented as mean±standard error of mean. * p<0.05.
Figure 9:
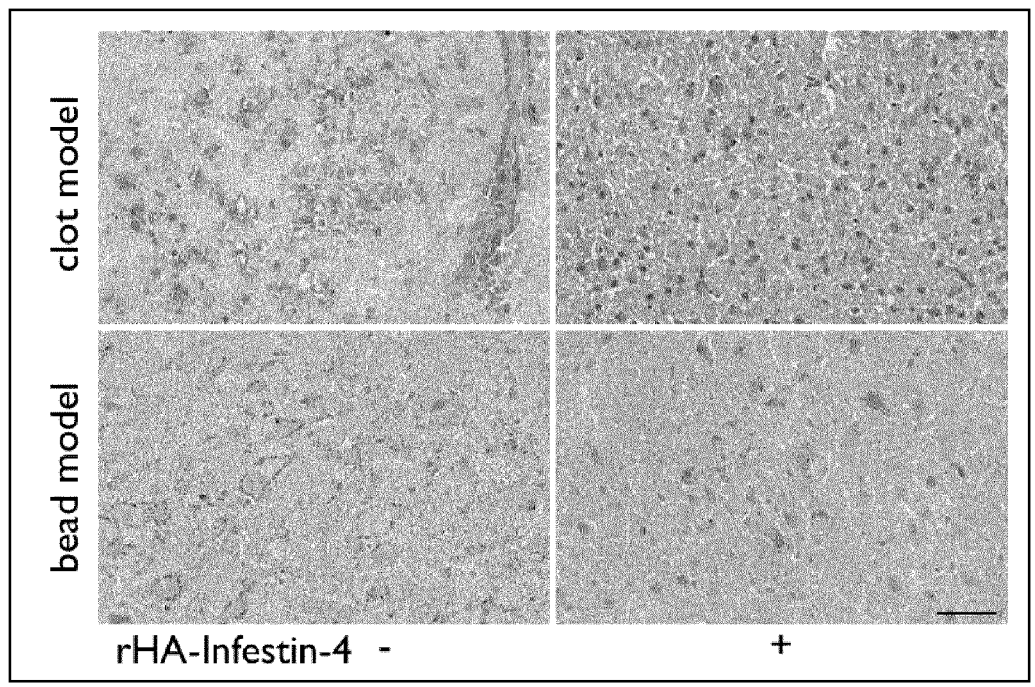
FIG. 9. Immunohistochemistry for FXIII. Immunohistochemical staining for FXIII 3 hours after administration of beads or coagulated blood. Bar indicates 50 μm.

To assess the effect of rHA-Infestin-4 on the coagulation cascade, the activity of FXIII was evaluated, which is downstream from and affected by FXII, and is responsible for cross-linking fibrin clots. In vivo SPECT-CT imaging was performed using the FXIII specific probe FXIII-Ind (Tung C H et al. 4 *Chembiochem.* 897-899, 2003; Nahrendorf M et al. 113 *Circulation* 1196-1202, 2006) during the acute stage after SBI induction. There was significant reduction in the amount of FXIII activity after rHA-Infestin-4 administration in both the coagulated blood (FIG. 7) and the microbead (FIG. 8) models. This was corroborated by autoradiography experiments on ex vivo brain specimens (FIGS. 7 and 8, middle panels). The overall degree of FXIII activity reduction is well visualized on the 3D fused images (FIGS. 7 and 8, left panels). Similar to the degree of infarct reduction, there was more pronounced reduction of FXIII activity in the coagulated blood model compared to the microbead model. In vivo imaging results were confirmed by immunohistochemical staining for FXIII (FIG. 9).

It is interesting to note that the microbeads model produced elevated factor XIII/coagulation activity that is diminished by rHA-Infestin-4 administration. This suggests that the microbead embolization caused fibrin clot formation, and induced secondary clotting due to tissue injury that may have caused further damage and occlusion of the affected vessels. Indeed, we found on histopathology that there is enhanced FXIII content in injured brain areas of untreated control mice (FIG. 9). Interestingly, the microbead model resulted in more injury and hemorrhagic areas compared to the coagulated blood model. One could speculate that the microbead model is more or less a permanent model, which aggravates the pathological effects, whereas the injected coagulated blood may be subject to (partial) thrombolysis leading to less severe outcome. Nevertheless, this secondary clot formation observed in both models can be significantly reduced by rHA-Infestin-4 to limit the damage from used embolized substances.

Example 5 rHA-Infestin-4 does not Alter Myeloperoxidase Activity in the Brain after SBI

Myeloperoxidase (MPO) is the most abundant enzyme secreted by many pro-inflammatory myeloid cells such as neutrophils, Ly6C$^{hi}$ monocytes, and subsets of activated macrophages and microglia during inflammation, and thus is a suitable imaging biomarker of the inflammatory response. To assess MPO activity, in vivo MRI was performed three days after SBI using the probe MPO-Gd (Chen J W et al. 240 *Radiology* 473-481, 2006; Querol M et al. 4 *Org Biomol Chem.* 1887-1895, 2006), that is highly specific and sensitive to MPO activity (Rodriguez E et al. 132 *J. Am. Chem. Soc.* 168-177, 2010; Ronald J A et al. 120 *Circulation* 592-599, 2009; Chen J W et al. 131 *Brain* 1123-1133, 2008; Breckwoldt M O et al. 105 *PNAS* 18584-18589, 2008; Nahrendorf M et al. 117 *Circulation* 1153-1160, 2008).

Figure 10:
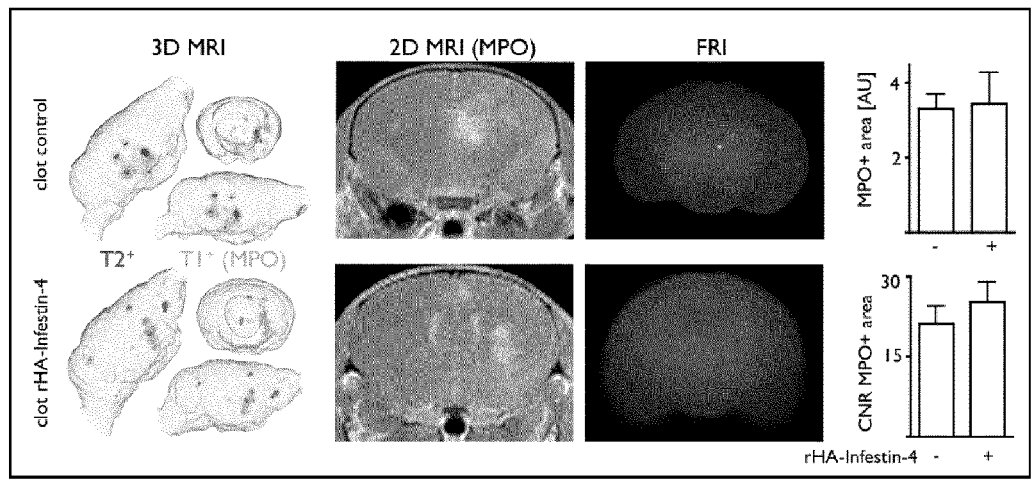
FIG. 10. No change in MPO activity measured by MRI after administration of coagulated blood. Assessment of MPO activity 3 days after administration of an embolus comprised of coagulated blood. FRI: Fluorescence reflectance imaging, showing location of coagulated blood. AU: Arbitrary units. CNR: Contrast to noise ratio. Data are presented as mean±standard error of mean. p>0.05.
Figure 11:
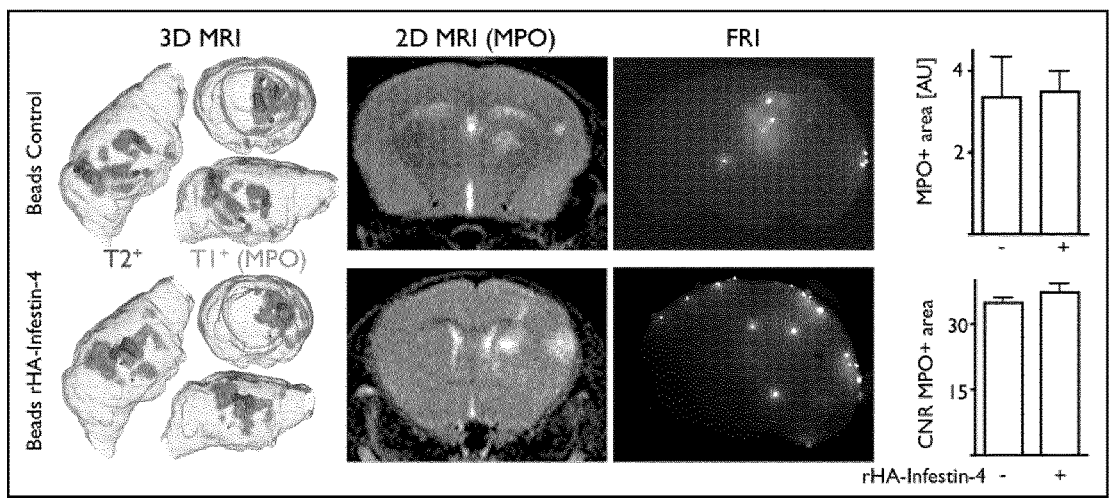
FIG. 11. No change in MPO activity measured by MRI after administration of microbeads. Assessment of MPO activity 3 days after administration of microbead emboli. FRI: Fluorescence reflectance imaging, showing position of beads. AU: Arbitrary units. CNR: Contrast to noise ratio. Data are presented as mean±standard error of mean. p>0.05.

There was more diffuse MPO activity affecting a larger volume compared to the infarcted areas as reported by T2-weighted imaging in both models (FIGS. 10 and 11, left panel, note there are more orange (MPO+ areas) compared to blue (T2 hyperintense foci) lesions, and right top panel, showing a T2 normalized MPO+ areas to be greater than unity). The microbead model induced more MPO activity when compared to the coagulated blood model (CNR, beads: 36±1, clots: 23±2, p<0.05) and larger lesions (number of T2+ voxels in the brain, beads: 3162±1435, clots: 548±207; p=0.05).

After rHA-Infestin-4 administration, there was not a significant change in the normalized areas of MPO+ lesions and the average CNR of all the MPO+ lesions in both SBI models, demonstrating that rHA-Infestin-4 does not affect MPO activity and thus myeloid cell activity. Therefore, despite a possible anti-inflammatory effect inferred from the function of FXII, rHA-Infestin-4 did not change the amount of MPO activity per lesion on day 3 post SBI induction. Day 3 was chosen for assessing MPO activity and inflammation because this time point was found to be the time point of maximal MPO activity in a stroke model (Breckwoldt M O et al. 105 *PNAS* 18584-18589, 2008). Thus, other parts of the inflammatory cascade may be affected by rHA-Infestin-4 that are not reflected in the MPO activity at day 3 (Breckwoldt M O et al. 105 *PNAS* 18584-18589, 2008). The majority of the inflammatory cells involved in cerebral ischemia are myeloid cells, therefore, even if other factors are affected by rHA-Infestin-4, the effect may be small.

The FXII inhibitor rHA-Infestin-4 may be used to treat an ischemic injury associated with various types of emboli that lead to SBI, without increasing the risk of bleeding in a patient or in an animal. In addition, said animal models and imaging approaches may be useful as tools to study mechanisms underlying the pathophysiology of SBI, and evaluate and monitor therapeutic candidates.

The invention claimed is:

1. A method of treating small ischemic injuries in a patient, comprising administering to the patient an effective amount of an inhibitor of Factor XII (FXII) to treat the small ischemic injuries, wherein the administering is performed before, during, and/or after a medical procedure in the patient comprising contact with at least one of:
   (a) the patient's heart,
   (b) at least one blood vessel in the patient chosen from: the aorta, the aortic arch, a carotid artery, a coronary artery, brachiocephalic artery, vertebrobasilar circulation, intracranial arteries, renal artery, a hepatic artery, a mesenteric artery, and/or a blood vessel of the arterial system cranial to the heart, and
   (c) a venous blood vessel in the patient if the patient has a known septal defect;
   wherein the medical procedure of (a), (b), and (c) comprises release of at least one microembolus in at least one of said heart and blood vessels of (a), (b), and (c) in the body.

2. The method according to claim 1, wherein the microembolus is comprised of bubbles, oil, fat, cholesterol, coagulated blood, and/or debris.

3. The method according to claim 1, wherein the medical procedure results in small ischemic injuries in at least one target organ comprising:
   (a) brain, wherein the patient has, has had, or is at risk for:
   (i) silent brain ischemia or
   (ii) a stroke caused by a nonthrombolysable substance; and/or
   (b) heart, kidney, liver, and/or a gastrointestinal tract organ.

4. The method according to claim 1, wherein the medical procedure comprises contact with the inside of at least one of said blood vessels.

5. The method according to claim 1, wherein the medical procedure comprises clamping of at least one of said blood vessels.

6. The method according to claim 1, wherein the medical procedure is a vascular procedure that comprises any one or more of a catheter, a stent, a balloon, a graft, and/or administering a contrast agent.

7. The method according to claim 1, wherein the medical procedure is a vascular surgery and/or is a vascular procedure that is diagnostic.

8. The method according to claim 1, wherein the medical procedure is coronary angiography, carotid artery stenting, percutaneous coronary intervention, carotid endarerectomy, a cardiovascular surgery, or dilation of stenotic renal artery.

9. The method according to claim 1, wherein the FXII inhibitor comprises
   (i) wild type Infestin-4 polypeptide sequence (SEQ ID NO: 1), or a variant thereof, wherein the variant comprises
   (a) the N-terminal amino acids 2-13 of the wild type Infestin-4 sequence (SEQ ID NO: 1) and at least one and up to five amino acid mutations outside said N-terminal amino acids that result in differences from the wild type Infestin-4 sequence, wherein said N-terminal amino acids 2-13 correspond to SEQ ID NO: 11; and/or
   (b) six conserved cysteine residues from the wild type Infestin-4 sequence and a homology of at least 70% to the wild type Infestin-4 sequence (SEQ ID NO: 1), (ii) SPINK-1 (SEQ ID NO: 2), which is mutated to include the N-terminal amino acids 2-13 of the wild type Infestin-4 sequence (SEQ ID NO: 1), or a variant of said mutated SPINK-1, wherein the variant comprises
  a) the N-terminal amino acids 2-13 of the wild type Infestin-4 sequence, and at least one and up to five amino acid mutations outside said N-terminal amino acids that result in differences from the wild type SPINK-1 sequence and which increase the homology of the variant to the wild type Infestin-4 sequence; and/or
  b) six conserved cysteine residues from the wild type SPINK-1 sequence and a homology of at least 70% to the wild type SPINK-1 sequence;
(iii) antithromin III (AT III), angiotensin converting enzyme inhibitor C1 inhibitor, aprotinin, alpha-1 protease inhibitor, antipain ([(S)-1Carboxy-2-Phenyl-ethyl]-Carbamoyl-L-Arg-L-Val-Arginal), Z-Pro-Pro-aldehyde-dimethyl acetate, DX88, leupeptin, Fmoc-Ala-Pyr-CN, corn-trypsin inhibitor, mutants of the bovine pancreatic trypsin inhibitor, ecotin, YAP (yellowfin sole anticoagulant protein), *Curcurbita maxima* trypsin inhibitor-V, *Curcurbita maxima* isoinhibitors and/or Pro-Phe-Arg-chloromethyl-ketone (PCK); or
(iv) an anti-FXII antibody, wherein the antibody binds to FXII and inhibits its activity and/or activation.

10. The method according to claim 9, wherein the variant of the mutated SPINK-1 is SPINK K1 (SEQ ID NO: 3), SPINK K2 (SEQ ID NO: 4), or SPINK K3 (SEQ ID NO: 5).

11. The method according to claim 1, wherein the FXII inhibitor is linked to a half-life enhancing polypeptide, wherein the half-life enhancing peptide comprises albumin, afamin, alpha-fetoprotein, vitamin D binding protein, human albumin or a variant thereof, an immunoglobulin or variant thereof, or an Fc of an IgG.

12. The method according to claim 11, wherein the half-life enhancing polypeptide is linked to the FXII inhibitor via a linker.

13. The method according to claim 12, wherein the linker is at least one of:
  (i) cleavable;
  (ii) cleavable by a coagulation protease of the intrinsic, extrinsic, or common coagulation pathway; and
  (iii) cleavable by FXIIa.

* * * * *

SEQUENCE LISTING

<160> NUMBER OF SEQ ID NOS: 12

<210> SEQ ID NO 1

<211> LENGTH: 48
<212> TYPE: PRT
<213> ORGANISM: Triatoma infestans

<400> SEQUENCE: 1

Glu Val Arg Asn Pro Cys Ala Cys Phe Arg Asn Tyr Val Pro Val Cys
1               5                   10                  15

Gly Ser Asp Gly Lys Thr Tyr Gly Asn Pro Cys Met Leu Asn Cys Ala
            20                  25                  30

Ala Gln Thr Lys Val Pro Gly Leu Lys Leu Val His Glu Gly Arg Cys
        35                  40                  45

<210> SEQ ID NO 2
<211> LENGTH: 56
<212> TYPE: PRT
<213> ORGANISM: Homo sapiens

<400> SEQUENCE: 2

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 3
<211> LENGTH: 53
<212> TYPE: PRT
<213> ORGANISM: Artificial sequence
<220> FEATURE:
<223> OTHER INFORMATION: Mutated human SPINK-1

<400> SEQUENCE: 3

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Pro Asn Glu Cys
            20                  25                  30

Val Leu Cys Phe Glu Asn Arg Lys Arg Gln Thr Ser Ile Leu Ile Gln
        35                  40                  45

Lys Ser Gly Pro Cys
    50

<210> SEQ ID NO 4
<211> LENGTH: 53
<212> TYPE: PRT
<213> ORGANISM: Artificial sequence
<220> FEATURE:
<223> OTHER INFORMATION: Mutated human SPINK-1

<400> SEQUENCE: 4

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
            20                  25                  30

Met Leu Cys Ala Glu Asn Arg Lys Arg Gln Thr Ser Ile Leu Ile Gln
        35                  40                  45

Lys Glu Gly Pro Cys
    50

-continued

<210> SEQ ID NO 5
<211> LENGTH: 54
<212> TYPE: PRT
<213> ORGANISM: Artificial sequence
<220> FEATURE:
<223> OTHER INFORMATION: Mutated human SPINK-1

<400> SEQUENCE: 5

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
                20                  25                  30

Met Leu Asn Cys Ala Glu Asn Arg Lys Arg Gln Thr Ser Ile Leu Ile
            35                  40                  45

Gln Lys Glu Gly Pro Cys
    50

<210> SEQ ID NO 6
<211> LENGTH: 585
<212> TYPE: PRT
<213> ORGANISM: Homo sapiens

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser

```
            260                 265                 270
Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 7
<211> LENGTH: 294
<212> TYPE: PRT
<213> ORGANISM: Artificial Sequence
<220> FEATURE:
<223> OTHER INFORMATION: Fusion Protein

<400> SEQUENCE: 7

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
                20                  25                  30

Met Leu Cys Ala Glu Asn Arg Lys Arg Gln Thr Ser Ile Leu Ile Gln
```

```
                    35                  40                  45
Lys Glu Gly Pro Cys Gly Gly Ser Gly Gly Ser Gly Gly Ser Glu Pro
 50                  55                  60

Lys Ser Cys Asp Lys Thr His Thr Cys Pro Pro Cys Pro Ala Pro Glu
 65                  70                  75                  80

Leu Leu Gly Gly Pro Ser Val Phe Leu Phe Pro Pro Lys Pro Lys Asp
                 85                  90                  95

Thr Leu Met Ile Ser Arg Thr Pro Glu Val Thr Cys Val Val Val Asp
                100                 105                 110

Val Ser His Glu Asp Pro Glu Val Lys Phe Asn Trp Tyr Val Asp Gly
                115                 120                 125

Val Glu Val His Asn Ala Lys Thr Lys Pro Arg Glu Glu Gln Tyr Asn
            130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
                180                 185                 190

Pro Gln Val Tyr Thr Leu Pro Pro Ser Arg Glu Glu Met Thr Lys Asn
            195                 200                 205

Gln Val Ser Leu Thr Cys Leu Val Lys Gly Phe Tyr Pro Ser Asp Ile
210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
            275                 280                 285

Ser Leu Ser Pro Gly Lys
            290

<210> SEQ ID NO 8
<211> LENGTH: 34
<212> TYPE: DNA
<213> ORGANISM: Artificial
<220> FEATURE:
<223> OTHER INFORMATION: Primer

<400> SEQUENCE: 8
gcggctagca tgaagtgggt aacctttatt tccc                               34

<210> SEQ ID NO 9
<211> LENGTH: 35
<212> TYPE: DNA
<213> ORGANISM: Artificial
<220> FEATURE:
<223> OTHER INFORMATION: Primer

<400> SEQUENCE: 9
gcgggatcct cctaagccta aggcagcttg acttg                              35

<210> SEQ ID NO 10
<211> LENGTH: 48
<212> TYPE: PRT
<213> ORGANISM: Rhodnius prolixus
```

```
<400> SEQUENCE: 10

Glu Gly Gly Glu Pro Cys Ala Cys Pro His Ala Leu His Arg Val Cys
1               5                   10                  15

Gly Ser Asp Gly Glu Thr Tyr Ser Asn Pro Cys Thr Leu Asn Cys Ala
            20                  25                  30

Lys Phe Asn Gly Lys Pro Glu Leu Val Lys Val His Asp Gly Pro Cys
        35                  40                  45

<210> SEQ ID NO 11
<211> LENGTH: 12
<212> TYPE: PRT
<213> ORGANISM: Artificial sequence
<220> FEATURE:
<223> OTHER INFORMATION: Fragment of human SPINK-1

<400> SEQUENCE: 11

Val Arg Asn Pro Cys Ala Cys Phe Arg Asn Tyr Val
1               5                   10

<210> SEQ ID NO 12
<211> LENGTH: 9
<212> TYPE: PRT
<213> ORGANISM: Artificial sequence
<220> FEATURE:
<223> OTHER INFORMATION: Linker

<400> SEQUENCE: 12

Gly Gly Ser Gly Gly Ser Gly Gly Ser
1               5
```